United States Patent
Conlon et al.

(10) Patent No.: US 8,864,717 B2
(45) Date of Patent: *Oct. 21, 2014

(54) SUBCUTANEOUS SELF ATTACHING INJECTION PORT WITH INTEGRAL MOVEABLE RETENTION MEMBERS

(75) Inventors: Sean P. Conlon, Loveland, OH (US); Richard P. Nuchols, Loveland, OH (US); John V. Hunt, Cincinnati, OH (US); Randal T. Byrum, South Lebanon, OH (US); Dale R. Schulze, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 207 days.

This patent is subject to a terminal disclaimer.

(21) Appl. No.: 12/966,236

(22) Filed: Dec. 13, 2010

(65) Prior Publication Data

US 2011/0082426 A1    Apr. 7, 2011

Related U.S. Application Data

(63) Continuation of application No. 10/741,875, filed on Dec. 19, 2003, now Pat. No. 7,862,546.

(60) Provisional application No. 60/478,763, filed on Jun. 16, 2003.

(51) Int. Cl.
*A61M 5/32* (2006.01)
*A61M 39/02* (2006.01)
*A61F 5/00* (2006.01)

(52) U.S. Cl.
CPC ... *A61M 39/0208* (2013.01); *A61M 2039/0223* (2013.01); *A61F 5/0056* (2013.01)
USPC .......................................................... 604/175

(58) Field of Classification Search
CPC ................... A61F 5/0056; A61M 2039/0223; A61M 39/0208
USPC ........ 604/174, 175, 228, 228.01, 228.04, 116
See application file for complete search history.

(56) References Cited

U.S. PATENT DOCUMENTS

| 2,737,954 A | 3/1956 | Knapp |
| 3,371,352 A | 3/1968 | Siposs et al. |
| 3,587,115 A | 6/1971 | Shiley |

(Continued)

FOREIGN PATENT DOCUMENTS

| AU | 2004281641 | 5/2010 |
| AU | 2006202145 | 12/2012 |

(Continued)

OTHER PUBLICATIONS

U.S. Appl. No. 60/478,763, filed Jun. 16, 2003, Conlon et al.

(Continued)

*Primary Examiner* — Emily Schmidt
*Assistant Examiner* — Michael J Anderson
(74) *Attorney, Agent, or Firm* — Frost Brown Todd LLC

(57) ABSTRACT

A self attaching injection port has integral moveable fasteners which are moveable from a undeployed state to a deployed state engaging tissue. The fasteners may be disposed radially or tangentially, and rotated to pierce the fascia. The fasteners may be rigid or elastically deformable.

19 Claims, 22 Drawing Sheets

(56) References Cited

U.S. PATENT DOCUMENTS

| | | |
|---|---|---|
| 3,686,740 A | 8/1972 | Shiley |
| 3,850,324 A | 11/1974 | Meyer |
| 4,378,023 A | 3/1983 | Trabucco |
| 4,543,088 A | 9/1985 | Bootman et al. |
| 4,569,675 A | 2/1986 | Prostl et al. |
| 4,592,339 A | 6/1986 | Kuzmak et al. |
| 4,621,640 A | 11/1986 | Mulhollan et al. |
| 4,665,906 A | 5/1987 | Jervis |
| 4,673,394 A | 6/1987 | Fenton, Jr. et al. |
| 4,685,447 A | 8/1987 | Iverson et al. |
| 4,692,146 A | 9/1987 | Hilger |
| 4,704,103 A | 11/1987 | Stober et al. |
| 4,710,174 A | 12/1987 | Moden et al. |
| 4,723,948 A | 2/1988 | Clark et al. |
| 4,732,948 A | 3/1988 | McCready et al. |
| 4,738,023 A | 4/1988 | Fabris |
| 4,738,657 A | 4/1988 | Hancock et al. |
| 4,762,517 A | 8/1988 | McIntyre et al. |
| 4,767,410 A | 8/1988 | Moden et al. |
| 4,772,261 A | 9/1988 | Von Hoff et al. |
| 4,772,270 A | 9/1988 | Wiita et al. |
| 4,778,452 A | 10/1988 | Moden et al. |
| 4,781,680 A | 11/1988 | Redmond et al. |
| 4,781,695 A | 11/1988 | Dalton |
| 4,798,584 A | 1/1989 | Hancock et al. |
| 4,802,885 A | 2/1989 | Weeks et al. |
| 4,834,720 A | 5/1989 | Blinkhorn |
| 4,840,615 A | 6/1989 | Hancock et al. |
| 4,861,341 A | 8/1989 | Woodburn |
| 4,880,414 A | 11/1989 | Whipple |
| 4,892,518 A | 1/1990 | Cupp et al. |
| 4,898,585 A | 2/1990 | Borsanyi et al. |
| 4,904,241 A | 2/1990 | Bark |
| 4,925,445 A | 5/1990 | Sakamoto et al. |
| 4,929,230 A | 5/1990 | Pfleger |
| 4,929,236 A | 5/1990 | Sampson |
| 4,969,873 A | 11/1990 | Steinbach et al. |
| 4,976,715 A | 12/1990 | Bays et al. |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melskky et al. |
| 5,053,013 A | 10/1991 | Ensminger et al. |
| 5,090,954 A | 2/1992 | Geary |
| 5,108,377 A | 4/1992 | Cone et al. |
| 5,123,199 A | 6/1992 | Lysohir et al. |
| 5,129,891 A | 7/1992 | Young |
| 5,133,753 A | 7/1992 | Bark et al. |
| 5,137,529 A | 8/1992 | Watson et al. |
| 5,158,547 A | 10/1992 | Doan et al. |
| 5,174,487 A | 12/1992 | Rothfuss et al. |
| 5,178,612 A | 1/1993 | Fenton, Jr. |
| 5,185,003 A | 2/1993 | Brethauer |
| 5,203,864 A | 4/1993 | Phillips |
| 5,207,644 A | 5/1993 | Strecker |
| 5,213,574 A | 5/1993 | Tucker |
| 5,217,486 A | 6/1993 | Rice et al. |
| 5,226,429 A | 7/1993 | Kuzmak |
| 5,246,156 A | 9/1993 | Rothfuss et al. |
| 5,261,914 A | 11/1993 | Warren |
| 5,263,930 A | 11/1993 | Ensminger |
| 5,279,564 A | 1/1994 | Taylor |
| 5,281,199 A | 1/1994 | Ensminger et al. |
| 5,290,297 A | 3/1994 | Phillips |
| 5,305,202 A | 4/1994 | Gallant et al. |
| 5,318,545 A | 6/1994 | Tucker |
| 5,324,518 A | 6/1994 | Orth et al. |
| 5,328,465 A | 7/1994 | Kratoska et al. |
| 5,332,398 A | 7/1994 | Miller et al. |
| 5,333,772 A | 8/1994 | Rothfuss et al. |
| 5,336,194 A | 8/1994 | Polaschegg |
| 5,350,360 A | 9/1994 | Ensminger et al. |
| 5,360,407 A | 11/1994 | Leonard et al. |
| 5,364,408 A | 11/1994 | Gordon |
| 5,381,943 A | 1/1995 | Allen et al. |
| 5,387,192 A | 2/1995 | Glantz et al. |
| 5,399,168 A | 3/1995 | Wadsworth, Jr. et al. |
| 5,417,656 A | 5/1995 | Ensminger et al. |
| 5,423,857 A * | 6/1995 | Rosenman et al. ............ 606/219 |
| 5,445,616 A | 8/1995 | Kratoska et al. |
| 5,464,407 A | 11/1995 | McGuire |
| 5,470,010 A | 11/1995 | Rothfuss et al. |
| 5,476,460 A | 12/1995 | Montalvo |
| 5,503,630 A | 4/1996 | Ensminger et al. |
| 5,527,277 A | 6/1996 | Ensminger et al. |
| 5,527,278 A | 6/1996 | Ensminger et al. |
| 5,527,321 A | 6/1996 | Hinchliffe |
| 5,540,648 A | 7/1996 | Yoon |
| 5,545,152 A | 8/1996 | Funderburk et al. |
| 5,558,641 A | 9/1996 | Glantz et al. |
| 5,562,618 A | 10/1996 | Cai et al. |
| 5,573,540 A | 11/1996 | Yoon |
| 5,582,616 A | 12/1996 | Bolduc et al. |
| 5,588,581 A | 12/1996 | Conlon et al. |
| 5,591,143 A | 1/1997 | Trombley, III et al. |
| 5,601,224 A | 2/1997 | Bishop et al. |
| 5,601,604 A | 2/1997 | Vincent |
| 5,602,224 A | 2/1997 | Vrckovnik et al. |
| 5,613,945 A | 3/1997 | Cai et al. |
| 5,632,729 A | 5/1997 | Cai et al. |
| 5,634,584 A | 6/1997 | Okorocha et al. |
| 5,635,718 A | 6/1997 | De Puydt et al. |
| 5,637,102 A | 6/1997 | Tolkoff et al. |
| 5,653,718 A | 8/1997 | Yoon |
| 5,681,330 A | 10/1997 | Hughett et al. |
| 5,683,447 A | 11/1997 | Bush et al. |
| 5,688,247 A * | 11/1997 | Haindl et al. ................. 604/175 |
| 5,700,272 A | 12/1997 | Gordon et al. |
| 5,716,370 A | 2/1998 | Williamson, IV et al. |
| 5,718,682 A | 2/1998 | Tucker |
| 5,743,873 A | 4/1998 | Cai et al. |
| 5,792,104 A | 8/1998 | Speckman et al. |
| 5,792,123 A | 8/1998 | Ensminger |
| 5,810,882 A | 9/1998 | Bolduc et al. |
| 5,817,062 A | 10/1998 | Flom et al. |
| 5,829,662 A | 11/1998 | Allen et al. |
| 5,830,221 A | 11/1998 | Stein et al. |
| 5,853,394 A | 12/1998 | Tolkoff et al. |
| 5,871,532 A | 2/1999 | Schroeppel |
| RE36,176 E | 3/1999 | Kuzmak |
| 5,902,598 A | 5/1999 | Chen et al. |
| 5,954,687 A | 9/1999 | Baudino |
| 5,976,159 A | 11/1999 | Bolduc et al. |
| 5,989,216 A | 11/1999 | Johnson et al. |
| 6,001,386 A | 12/1999 | Ashton et al. |
| 6,086,555 A | 7/2000 | Eliasen et al. |
| 6,102,922 A | 8/2000 | Jakobsson et al. |
| 6,213,973 B1 | 4/2001 | Eliasen et al. |
| 6,251,090 B1 | 6/2001 | Avery et al. |
| 6,290,702 B1 | 9/2001 | Fucci et al. |
| 6,319,226 B1 | 11/2001 | Sherry |
| 6,447,524 B1 | 9/2002 | Knodel et al. |
| 6,461,292 B1 | 10/2002 | Forsell |
| 6,470,892 B1 | 10/2002 | Forsell |
| 6,478,783 B1 | 11/2002 | Moorehead |
| 6,511,490 B2 | 1/2003 | Robert |
| 6,527,754 B1 | 3/2003 | Tallarida et al. |
| 6,540,717 B2 | 4/2003 | Sherry |
| 6,556,857 B1 | 4/2003 | Estes et al. |
| 6,592,571 B1 | 7/2003 | Verbeek et al. |
| 6,607,504 B2 | 8/2003 | Haarala et al. |
| 6,827,722 B1 | 12/2004 | Schoenefeld |
| 6,962,577 B2 | 11/2005 | Tallarida et al. |
| 6,976,159 B1 | 12/2005 | Poduska et al. |
| 6,988,987 B1 | 1/2006 | Ishikawa et al. |
| 7,033,335 B2 | 4/2006 | Haarala et al. |
| 7,076,309 B2 | 7/2006 | Hine et al. |
| 7,097,770 B2 | 8/2006 | Lysenko et al. |
| 7,138,179 B2 | 11/2006 | Kim et al. |
| 7,152,601 B2 | 12/2006 | Barakat et al. |
| 7,152,926 B2 | 12/2006 | Wrobel |
| 7,195,774 B2 | 3/2007 | Carvalho et al. |

(56) References Cited

U.S. PATENT DOCUMENTS

| | | | |
|---|---|---|---|
| 7,223,239 B2 | 5/2007 | Schulze et al. | |
| 7,241,632 B2 | 7/2007 | Yang | |
| 7,341,577 B2 | 3/2008 | Gill | |
| 7,374,557 B2 | 5/2008 | Conlon et al. | |
| 7,387,635 B2 | 6/2008 | Keller | |
| 7,442,165 B2 | 10/2008 | Forsell | |
| 7,553,298 B2 | 6/2009 | Hunt et al. | |
| 7,561,916 B2 | 7/2009 | Hunt et al. | |
| 7,590,452 B2 | 9/2009 | Imran et al. | |
| 7,608,080 B2 | 10/2009 | Shipp et al. | |
| 7,621,863 B2 | 11/2009 | Forsell | |
| 7,651,483 B2 | 1/2010 | Byrum et al. | |
| 7,762,998 B2 | 7/2010 | Birk et al. | |
| 7,762,999 B2 | 7/2010 | Byrum | |
| 7,806,876 B2 | 10/2010 | Sherry | |
| 7,850,660 B2 | 12/2010 | Uth et al. | |
| 7,862,546 B2 * | 1/2011 | Conlon et al. | 604/175 |
| 8,007,479 B2 | 8/2011 | Birk et al. | |
| 8,007,747 B2 | 8/2011 | Giter et al. | |
| 8,029,477 B2 | 10/2011 | Byrum et al. | |
| 8,079,989 B2 | 12/2011 | Birk et al. | |
| 8,162,897 B2 | 4/2012 | Byrum | |
| 8,211,127 B2 | 7/2012 | Uth et al. | |
| 2003/0181890 A1 | 9/2003 | Schulze et al. | |
| 2004/0068233 A1 | 4/2004 | DiMatteo | |
| 2004/0093056 A1 | 5/2004 | Johnson et al. | |
| 2004/0199129 A1 | 10/2004 | DiMatteo | |
| 2004/0220682 A1 | 11/2004 | Levine et al. | |
| 2004/0249362 A1 | 12/2004 | Levine et al. | |
| 2005/0131352 A1 | 6/2005 | Conlon et al. | |
| 2005/0148956 A1 | 7/2005 | Conlon et al. | |
| 2005/0277899 A1 | 12/2005 | Conlon et al. | |
| 2005/0283119 A1 | 12/2005 | Uth et al. | |
| 2006/0178647 A1 | 8/2006 | Stats | |
| 2006/0190039 A1 * | 8/2006 | Birk et al. | 606/219 |
| 2006/0217668 A1 | 9/2006 | Schulze et al. | |
| 2006/0217673 A1 | 9/2006 | Schulze et al. | |
| 2006/0234445 A1 | 10/2006 | Yang | |
| 2006/0293626 A1 | 12/2006 | Byrum et al. | |
| 2007/0208313 A1 | 9/2007 | Conlon et al. | |
| 2007/0255306 A1 | 11/2007 | Conlon et al. | |
| 2007/0293829 A1 | 12/2007 | Conlon et al. | |
| 2010/0217199 A1 | 8/2010 | Uth et al. | |
| 2010/0217200 A1 | 8/2010 | Uth et al. | |
| 2010/0234808 A1 | 9/2010 | Uth et al. | |
| 2010/0286649 A1 | 11/2010 | Birk et al. | |
| 2011/0152901 A1 | 6/2011 | Woodruff et al. | |

FOREIGN PATENT DOCUMENTS

| | | |
|---|---|---|
| CN | 1600281 A | 3/2005 |
| DE | 42 11 045 | 10/1993 |
| DE | 197 45 654 | 4/1999 |
| DE | 197 51 791 | 5/1999 |
| EP | 0 858 814 | 8/1998 |
| EP | 1 057 457 | 12/2000 |
| EP | 1 346 753 | 9/2003 |
| EP | 1 488 824 | 12/2004 |
| EP | 1 662 971 | 6/2006 |
| EP | 1 670 362 | 6/2006 |
| EP | 1 676 527 | 7/2006 |
| EP | 1 704 891 | 9/2006 |
| EP | 1 736 123 | 12/2006 |
| EP | 1 736 197 | 12/2006 |
| EP | 1 736 198 | 12/2006 |
| EP | 1 832 252 | 9/2007 |
| JP | 62-281966 | 12/1987 |
| JP | 2-119877 | 5/1990 |
| JP | 03-275075 | 12/1991 |
| JP | 8-107934 | 4/1996 |
| JP | 2000-093524 | 4/2000 |
| JP | 2005-007171 | 1/2005 |
| JP | 2007-505696 | 3/2007 |
| RU | 1823791 | 11/2006 |
| SU | 1823791 | 6/1993 |
| WO | WO 94/22520 | 10/1994 |
| WO | WO 96/40357 | 12/1996 |
| WO | WO 97/01370 | 1/1997 |
| WO | WO 97/30659 | 8/1997 |
| WO | WO 99/26543 | 6/1999 |
| WO | WO 99/34859 | 7/1999 |
| WO | WO 00/33901 | 6/2000 |
| WO | WO 01/80926 | 11/2001 |
| WO | WO 02/053220 | 7/2002 |
| WO | WO 02/743810 | 9/2002 |
| WO | WO 2004/026152 | 4/2004 |
| WO | WO 2005/037055 | 4/2005 |
| WO | WO 2005/072627 | 8/2005 |

OTHER PUBLICATIONS

U.S. Appl. No. 60/503,074, filed Sep. 15, 2003, Birk et al.
Australian Search Report dated Aug. 31, 2007 for Application No. SG200604149-5.
Australian Search Report and Written Opinion dated Nov. 20, 2007 for Application No. SG200604066.
EPO Search Report dated Aug. 19, 2004 for Application No. 04253581.
EPO Search Report dated Oct. 4, 2005 for Application No. 05253363.
EPO Search Report dated Oct. 4, 2006 for Application No. 06253285.
EPO Search Report dated Oct. 16, 2006 for Application No. 06253284.
EPO Search Report dated Nov. 17, 2006 for Application No. 06253284.
Partial EPO Search Report dated Oct. 30, 2006 for Application No. 06253276.
Examination Report dated Nov. 24, 2006 for Application No. 04253581.
Extended EPO Search Report dated Jan. 16, 2007 for Application No. 06253276.
Examination Report dated Oct. 22, 2007 for Application No. 04253581.
Examination Report dated Nov. 30, 2006 for Application No. 05253363.
Examination Report dated Jan. 18, 2008 for Application No. 05253363.
Examination Report dated Jul. 10, 2008 for Application No. 05253363.
Examination Report dated Jan. 15, 2009 for Application No. 04253581.
Abstract for DE 42 11 045.
Abstract for EP 0 858 814.
Australian Search Report dated Jul. 16, 2007 for Singaporean Application No. SG 200604063.
Australian Search Report dated Sep. 7, 2007 for Singaporean Application No. SG 206604149.
Australian Examiner's Report dated Apr. 22, 2010 for Application No. AU 2005202292.
Australian Examiner's Report dated Mar. 19, 2012 for Application No. AU 2006202145.
Austrian Written Opinion dated Nov. 30, 2007 for Singaporean Application No. SG 200604066.
European Patent Office Opposition Decision dated Feb. 4, 2011 for Application No. EP 06253277.
Response in Appeal of Opposition Decision from European Patent Office dated Nov. 8, 2011 for Application No. EP 06253277.
European Search Report dated Oct. 13, 2006 for Application No. 06253285.
Japanese Office Action dated Dec. 24, 2010 for Application No. JP 2005-160203.
Abstract and English Machine Translation of Japanese Patent No. JP 2000-093524.
Office Action dated Dec. 27, 2010 for U.S. Appl. No. 11/471,767.
Office Action dated Jun. 9, 2011 for U.S. Appl. No. 11/471,767.
Notice of Allowance dated Sep. 21, 2011 for U.S. Appl. No. 11/471,767.
Notice of Allowance dated Jan. 27, 2012 for U.S. Appl. No. 11/471,767.

(56) References Cited

OTHER PUBLICATIONS

Notice of Allowance dated Jul. 11, 2012 for U.S. Appl. No. 12/770,047.
Restriction Requirement dated Jun. 24, 2011 for U.S. Appl. No. 12/769,890.
Office Action dated Aug. 15, 2011 for U.S. Appl. No. 12/769,890.
Notice of Allowance dated Mar. 7, 2012 for U.S. Appl. No. 12/769,890.
Office Action dated Apr. 5, 2011 for U.S. Appl. No. 12/769,914.
Office Action dated Oct. 4, 2011 for U.S. Appl. No. 12/769,914.
Office Action dated Apr. 5, 2011 for U.S. Appl. No. 12/769,929.
Ex Parte Quayle Action dated Oct. 18, 2011 for U.S. Appl. No. 12/769,929.
Restriction Requirement dated Aug. 28, 2006 for U.S. Appl. No. 10/741,875.
Office Action dated Nov. 2, 2006 for U.S. Appl. No. 10/741,875.
Office Action dated Jun. 25, 2007 for U.S. Appl. No. 10/741,875.
Office Action dated Dec. 17, 2007 for U.S. Appl. No. 10/741,875.
Office Action dated May 27, 2008 for U.S. Appl. No. 10/741,875.
Office Action dated Oct. 27, 2008 for U.S. Appl. No. 10/741,875.
Office Action dated Mar. 20, 2009 for U.S. Appl. No. 10/741,875.
Office Action dated Oct. 2, 2009 for U.S. Appl. No. 10/741,875.
Notice of Allowance dated Apr. 9, 2010 for U.S. Appl. No. 10/741,875.
Notice of Allowance dated Sep. 1, 2010 for U.S. Appl. No. 10/741,875.
Office Action dated May 16, 2007 for U.S. Appl. No. 11/166,625.
Office Action dated Oct. 22, 2007 for U.S. Appl. No. 11/166,625.
Office Action dated Jan. 14, 2008 for U.S. Appl. No. 11/166,625.
Office Action dated Jul. 23, 2008 for U.S. Appl. No. 11/166,625.
Office Action dated Mar. 20, 2009 for U.S. Appl. No. 11/166,625.
Office Action dated Sep. 3, 2009 for U.S. Appl. No. 11/166,625.
Office Action dated Mar. 19, 2010 for U.S. Appl. No. 11/166,625.
Office Action dated Mar. 29, 2011 for U.S. Appl. No. 11/166,625.
Notice of Allowance dated May 16, 2011 for U.S. Appl. No. 11/166,625.
Office Action dated Apr. 12, 2007 for U.S. Appl. No. 11/166,610.
Office Action dated Oct. 17, 2007 for U.S. Appl. No. 11/166,610.
Office Action dated Jan. 15, 2008 for U.S. Appl. No. 11/166,610.
Office Action dated Jul. 14, 2008 for U.S. Appl. No. 11/166,610.
Office Action dated Dec. 29, 2008 for U.S. Appl. No. 11/166,610.
Office Action dated Jun. 3, 2009 for U.S. Appl. No. 11/166,610.
Notice of Allowance dated Jan. 15, 2010 for U.S. Appl. No. 11/166,610.
Notice of Allowance dated Feb. 1, 2010 for U.S. Appl. No. 11/166,610.
Notice of Allowance dated Sep. 7, 2010 for U.S. Appl. No. 11/166,610.
Restriction Requirement dated Nov. 27, 2006 for U.S. Appl. No. 10/741,868.
Office Action dated Mar. 7, 2007 for U.S. Appl. No. 10/741,868.
Office Action dated Sep. 7, 2007 for U.S. Appl. No. 10/741,868.
Notice of Allowance dated Jan. 14, 2008 for U.S. Appl. No. 10/741,868.
Office Action dated Feb. 27, 2008 for U.S. Appl. No. 11/166,611.
Office Action dated Jul. 31, 2008 for U.S. Appl. No. 11/166,611.
Office Action dated Oct. 20, 2008 for U.S. Appl. No. 11/166,611.
Notice of Allowance dated May 19, 2009 for U.S. Appl. No. 11/166,611.
Notice of Allowance dated Sep. 25, 2009 for U.S. Appl. No. 11/166,611.
Office Action dated Aug. 15, 2007 for U.S. Appl. No. 11/166,283.
Office Action dated Jan. 8, 2008 for U.S. Appl. No. 11/166,283.
Notice of Allowance dated Jun. 17, 2008 for U.S. Appl. No. 11/166,283.
Notice of Allowance dated Nov. 3, 2008 for U.S. Appl. No. 11/166,283.
Notice of Allowance dated Mar. 4, 2009 for U.S. Appl. No. 11/166,283.
Office Action dated Aug. 10, 2007 for U.S. Appl. No. 11/166,702.

Office Action dated Jan. 8, 2008 for U.S. Appl. No. 11/166,702.
Office Action dated Sep. 25, 2008 for U.S. Appl. No. 11/166,702.
Office Action dated Feb. 13, 2009 for U.S. Appl. No. 11/166,702.
Office Action dated May 14, 2009 for U.S. Appl. No. 11/166,702.
Office Action dated Dec. 4, 2009 for U.S. Appl. No. 11/166,702.
Office Action dated Jun. 7, 2010 for U.S. Appl. No. 11/166,702.
Notice of Allowance dated Dec. 13, 2010 for U.S. Appl. No. 11/166,702.
Office Action dated Jul. 23, 2007 for U.S. Appl. No. 11/166,968.
Restriction Requirement dated Jan. 2, 2008 for U.S. Appl. No. 11/166,968.
Office Action dated Apr. 18, 2008 for U.S. Appl. No. 11/166,968.
Office Action dated Sep. 8, 2008 for U.S. Appl. No. 11/166,968.
Restriction Requirement dated Feb. 13, 2009 for U.S. Appl. No. 11/166,968.
Notice of Allowance dated Apr. 6, 2009 for U.S. Appl. No. 11/166,968.
Office Action dated Jul. 12, 2007 for U.S. Appl. No. 10/858,614.
Office Action dated Nov. 14, 2007 for U.S. Appl. No. 10/858,614.
Office Action dated Mar. 31, 2008 for U.S. Appl. No. 10/858,614.
Office Action dated Nov. 13, 2008 for U.S. Appl. No. 10/858,614.
Office Action dated Apr. 15, 2009 for U.S. Appl. No. 10/858,614.
Office Action dated Oct. 27, 2009 for U.S. Appl. No. 10/858,614.
Office Action dated Mar. 28, 2007 for U.S. Appl. No. 10/741,127.
Office Action dated Sep. 11, 2007 for U.S. Appl. No. 10/741,127.
Office Action dated Jan. 8, 2008 for U.S. Appl. No. 10/741,127.
Office Action dated Jul. 7, 2008 for U.S. Appl. No. 10/741,127.
Australian Examiner's Report dated May 17, 2013 for Application No. AU 2012254952.
Canadian Office Action dated May 22, 2013 for Application No. CA 2508648.
Japanese Office Action dated Aug. 6, 2013 for Application No. JP 2007-162956.
Office Action Final dated Sep. 30, 2013 for U.S. Appl. No. 12/769,914.
Notice of Allowance dated Oct. 1, 2013 for U.S. Appl. No. 12/769,929.
U.S. Appl. No. 12/769,883, filed Apr. 29, 2010.
European Search Report dated Apr. 26, 2011 for Application No. 10177441.
European Search Report dated Mar. 31, 2011 for Application No. 10177808.
European Search Report dated Oct. 4, 2006 for Application No. 06253277.
European Search Report dated Oct. 18, 2007 for Application No. 07252500.
Partial European Search Report dated Sep. 27, 2006 for Application No. 06253283.
Partial European Search Report dated Aug. 4, 2009 for Application No. 08251093.
EPO Notice of Opposition to a European Patent dated Sep. 2, 2009 for European Application No. and Patent No. 06 253 277.5 / 1 736 197.
EPO Response to Attend Oral Proceedings dated Nov. 8, 2010 for European Application No. And Patent No. 06 253 277.5 / 1 736 197.
European Examination report dated Mar. 4, 2009 for Application No. 06 253 283.3.
Australian Examiner's Report dated Feb. 25, 2011 for Application No. AU 2006202145.
Australian Examiner's Report dated Jun. 2, 2009 for Application No. AU 2004202549.
Australian Examiner's Report dated Feb. 18, 2011 for Application No. AU 2006202115.
Australian Examiner's Report dated Sep. 27, 2011 for Application No. AU 2011200887.
Australian Examiner's Report dated Dec. 21, 2011 for Application No. AU 2011200887.
Australian Examiner's Report dated Apr. 18, 2012 for Application No. AU 2007202311.
Canadian Office Action dated Apr. 11, 2011 for Application No. CA 2471185.
Canadian Office Action dated Nov. 9, 2011 for Application No. CA 2508648.

(56) References Cited

OTHER PUBLICATIONS

Canadian Office Action dated Sep. 19, 2012 for Application No. CA 2508648.
Canadian Office Action dated Nov. 7, 2012 for Application No. CA 2549219.
Canadian Office Action dated Nov. 6, 2012 for Application No. CA 2549241.
Canadian Office Action dated Mar. 19, 2013 for Application No. CA 2590827.
Chinese Office Action dated Apr. 20, 2007 for Application No. CN 200410069447.0.
Chinese Office Action dated Jan. 12, 2012 for Application No. CN 200610093155X.
Chinese Office Action dated Dec. 22, 2011 for Application No. CN 200610093156.4.
Chinese Office Action dated Apr. 19, 2012 for Application No. CN 200610093156.4.
Chinese Office Action dated Jun. 22, 2010 for Application No. CN 200710112538.1.
Chinese Office Action dated Jul. 6, 2011 for Application No. CN 200710112538.1.
Chinese Office Action dated Apr. 5, 2012 for Application No. CN 200710112538.1.
Israeli Office Action dated Dec. 8, 2009 for Application No. IL 175828.
Israeli Office Action dated Dec. 14, 2009 for Application No. IL 175851.
Japanese Office Action dated Nov. 8, 2011 for Application No. JP 2005-160203.
Japanese Office Action dated Dec. 14, 2006 for Application No. JP 2004-177065.
Japanese Office Action dated Jun. 25, 2010 for Application No. JP 2004-177065.
Japanese Office Action dated Feb. 23, 2011 for Application No. JP 2004-177065.
Japanese Office Action dated Sep. 29, 2011 for Application No. JP 2006-174158.
Japanese Office Action dated Apr. 25, 2011 for Application No. JP 2006-174171.
Japanese Office Action dated Jun. 8, 2012 for Application No. JP 2007-162956.
Japanese Office Action dated Feb. 28, 2013 for Application No. JP 2007-162956.
Korean Office Action dated Oct. 21, 2011 for Application No. KR 10-2005-0045990.
Korean Office Action dated Dec. 18, 2012 for Application No. KR 10-2006-0056843.
Korean Office Action dated Dec. 19, 2012 for Application No. KR 10-2006-0056844.
Mexican Office Action dated Mar. 30, 2007 for Application No. PA/A/2004/005756.
Mexican Office Action dated May 14, 2009 for Application No. PA/A/2006/007379.
Mexican Office Action dated Nov. 20, 2009 for Application No. PA/A/2006/007379.
Mexican Office Action dated Nov. 7, 2011 for Application No. PA/A/2005/005810.
Mexican Office Action dated Oct. 16, 2009 for Application No. MX/A/2007/007468.
Russian Office Action dated May 20, 2009 for Application No. RU 2005116666.
Russian Office Action dated Apr. 28, 2010 for Application No. RU 2006122615.
Singaporean Office Action dated Oct. 31, 2007 for Application No. SG 200604117-2.

* cited by examiner

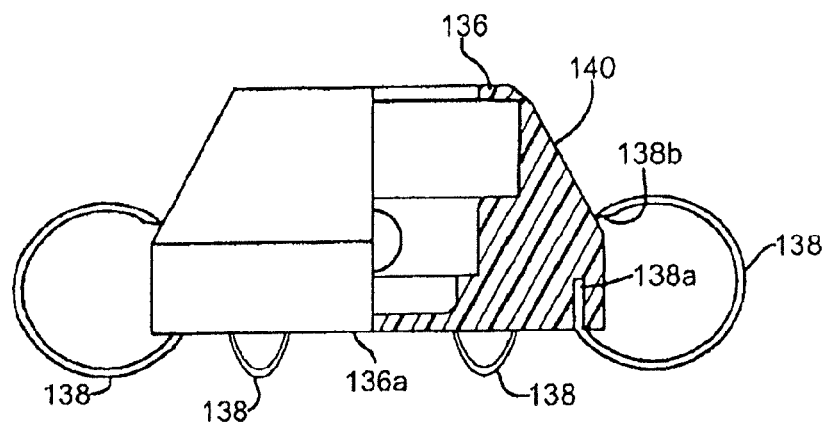
FIG. 27
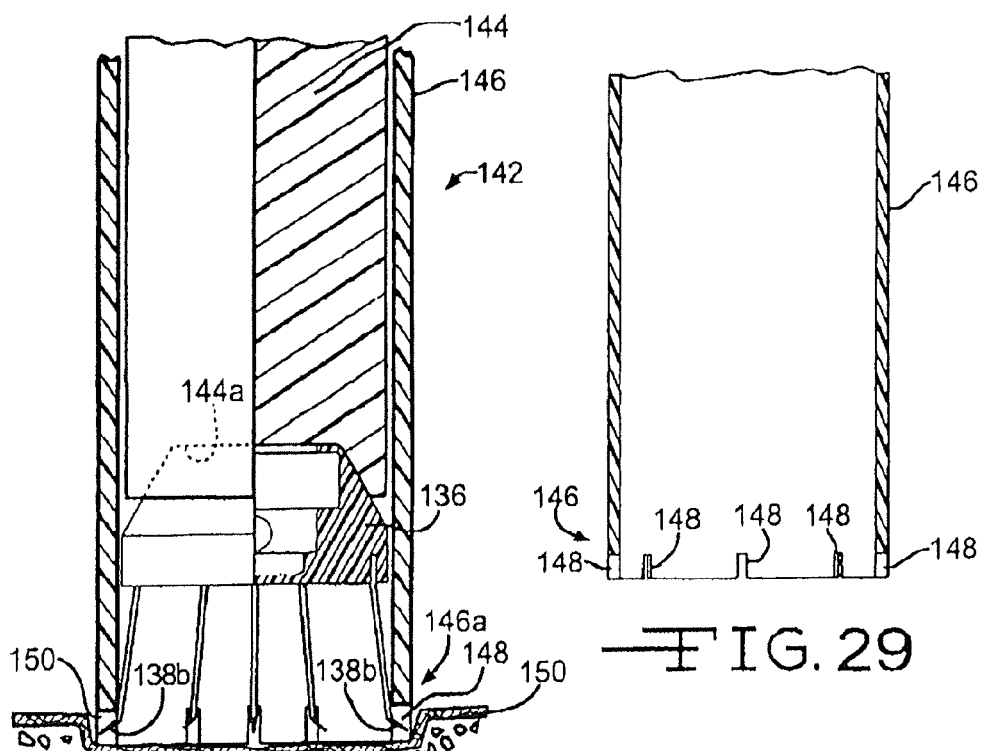
FIG. 28
FIG. 29

SUBCUTANEOUS SELF ATTACHING INJECTION PORT WITH INTEGRAL MOVEABLE RETENTION MEMBERS

RELATED APPLICATIONS

This application is a continuation of U.S. patent application Ser. No. 10/741,875, entitled "Subcutaneous Self Attaching Injection Port with Integral Moveable Retention Members," filed Dec. 19, 2003, now U.S. Pat. No. 7,862,546, which claims the priority of U.S. Provisional Patent Application Ser. No. 60/478,763, entitled "Fluid Injection Port For Adjustable Gastric Band," filed Jun. 16, 2003, the disclosure of which is incorporated herein by reference.

This application also incorporates by reference the following United States Patent Applications: U.S. patent application Ser. No. 10/741,127, filed Dec. 19, 2003, entitled "Subcutaneous Injection Port for Applied Fasteners," published as U.S. Patent Publication No. 2005/0131352; and U.S. patent application Ser. No. 10/741,868, filed Dec. 19, 2003, entitled "Subcutaneous Self Attaching Injection Port With Integral Fasteners," now U.S. Pat. No. 7,374,557.

TECHNICAL FIELD

The present invention relates in general to surgically implantable fluid injection ports, and is particularly directed to fasteners and methods for fastening subcutaneous peripherally attached ports. The invention will be specifically disclosed in connection with injection ports used with adjustable gastric bands, although the fasteners of the present invention may be used with many different subcutaneously attached devices, including injection ports used for vascular access such as the infusion of medications and blood draws.

BACKGROUND OF THE INVENTION

Injection ports are placed beneath the skin of a body for injecting fluids into the body, such as for infusing medication, blood draws, and many other applications, including adjustable gastric bands. Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

In addition to a latched position to set the outer diameter of the gastric band, adjustability of gastric bands is generally achieved with an inwardly directed inflatable balloon, similar to a blood pressure cuff, into which fluid, such as saline, is injected through a fluid injection port to achieve a desired diameter. Since adjustable gastric bands may remain in the patient for long periods of time, the fluid injection port is typically installed subcutaneously to avoid infection, for instance in front of the sternum. Adjusting the amount of fluid in the adjustable gastric band is achieved by inserting a Huber needle through the skin into a silicon septum of the injection port. Once the needle is removed, the septum seals against the hole by virtue of compressive load generated by the septum. A flexible conduit communicates between the injection port and the adjustable gastric band.

BRIEF SUMMARY OF THE INVENTION

As described herein, there is provided an injection port for injecting fluids into a body. The port includes a housing for placement beneath the skin of the body and means for receiving a needle. At least one retention member is integrally attached to the housing which is moveable with respect thereto. The retention member has an undeployed state when disposed in a first position relative to the housing and a deployed state engaging tissue adjacent the housing when disposed in a second position relative to the housing.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 6 is an exploded view of the injection port attachment assembly of FIG. 5;

FIG. 7 is a cross sectional view of the base taken along line 7-7 of FIG. 6;

FIG. 27 is a side view in partial cross section of another embodiment of an injection port with integral moveable retention members;

FIG. 28 is a cross-section side view an applier loaded with the injection port of FIG. 27 immediately prior to implantation;

FIG. 29 is a cross-section side view of the outer tube of the applier for implanting the injection port shown in FIG. 28;

DETAILED DESCRIPTION OF AN EMBODIMENT OF THE PRESENT INVENTION

Figure 1:
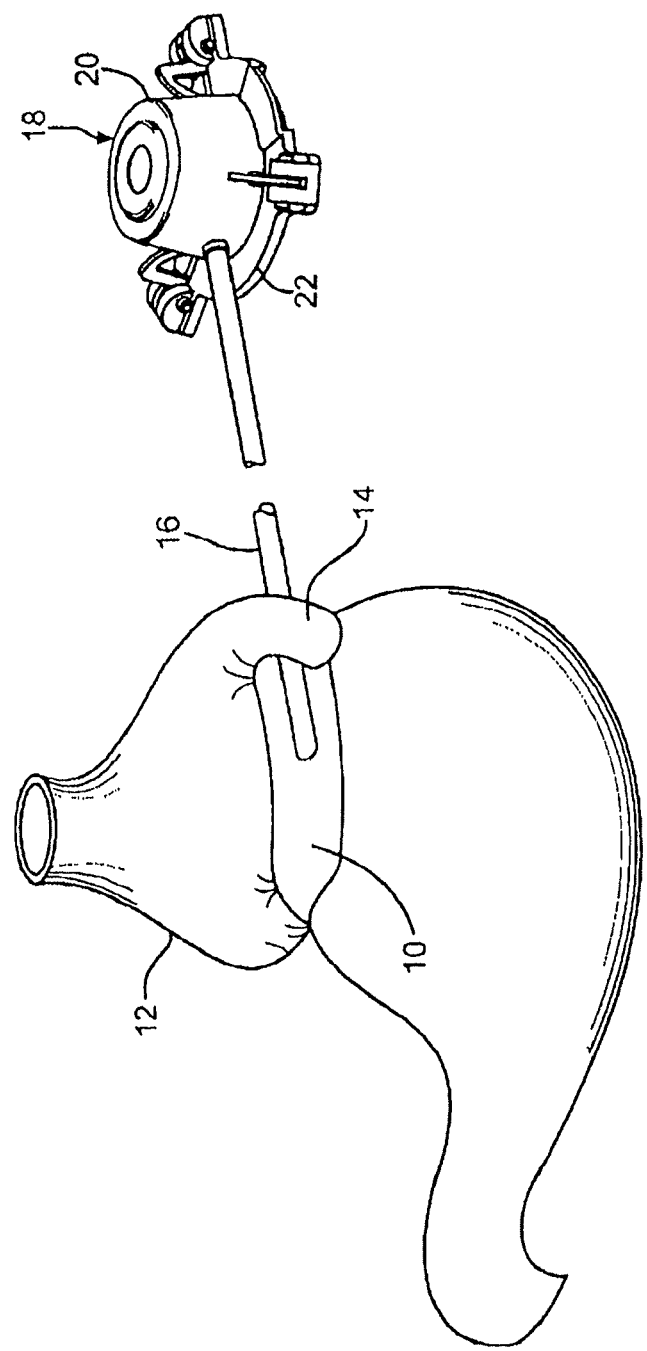
FIG. 1 is a diagrammatic drawing showing an injection port constructed in accordance with the present invention, connected to an adjustable gastric band wrapped around an upper part of a stomach.

Referring now to the drawings in detail, wherein like numerals indicate the same elements throughout the views, FIG. 1, adjustable gastric band 10 is shown wrapped around an upper portion of stomach 12, kept in place by attaching the two ends together and extending portion 14 of the stomach 12 over adjustable gastric band 10 by suturing portion 14 to the stomach. One end of flexible conduit 16 is in fluid communication with the internal cavity of the balloon (not shown), with the other end being in fluid communication with an internal cavity of injection port 18. At the time adjustable gastric band 10 is implanted around a portion of the stomach, remote injection port 18 is also implanted at a suitable location, usually within the rectus sheaths, for transcutaneous access via a Huber needle.

Figure 2:
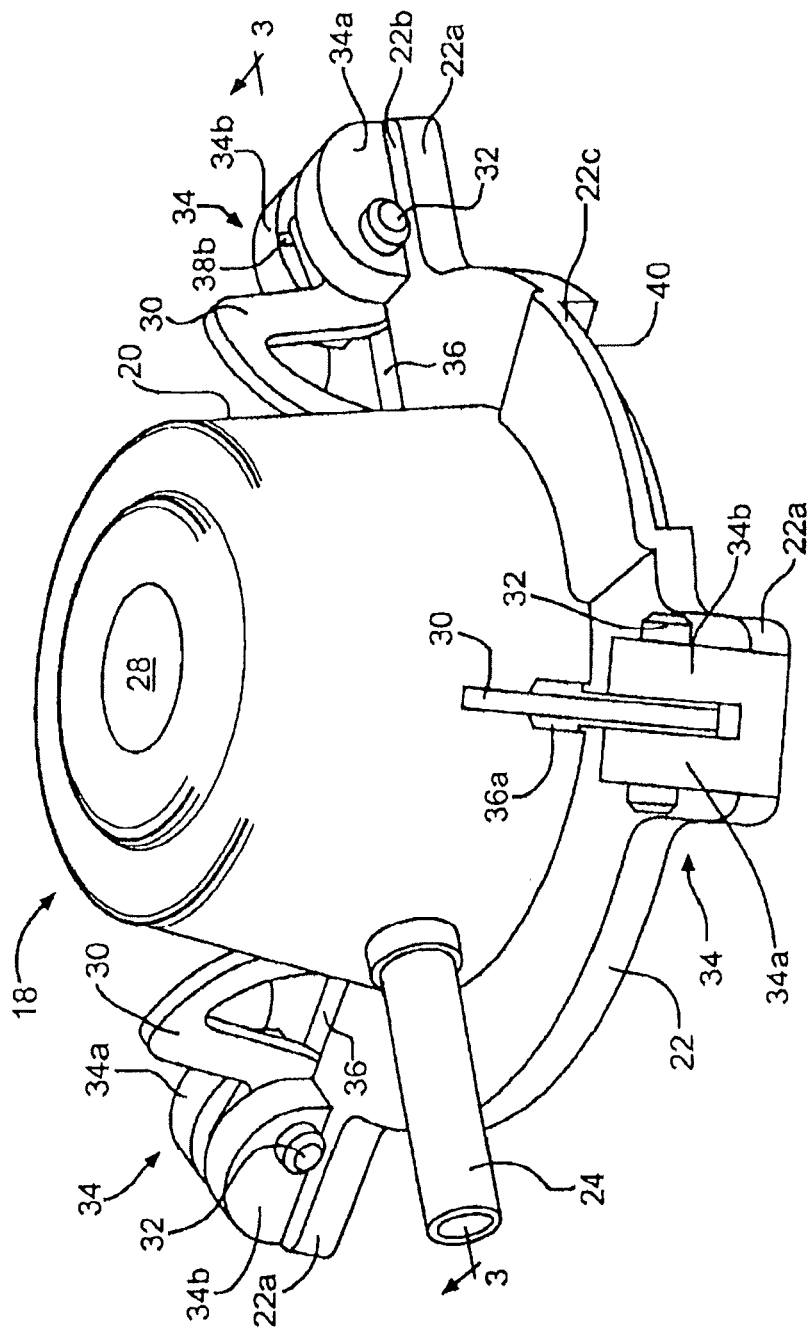
FIG. 2 is a perspective view of the injection port shown in FIG. 1.
Figure 3:
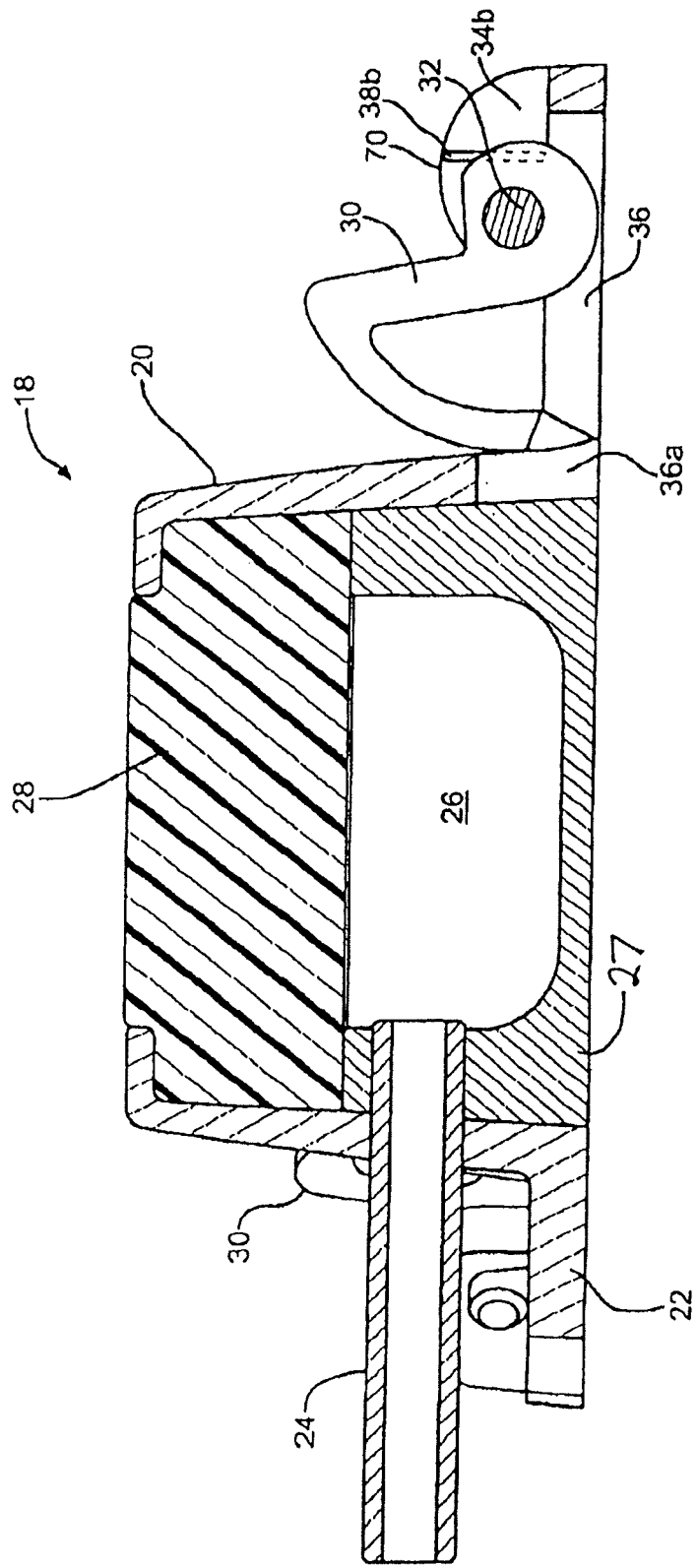
FIG. 3 is an enlarged, cross sectional view taken along a vertical plane through line 3-3 in FIG. 2.

Referring also to FIGS. 2 and 3, as is well known, injection port 18 includes housing 20 having annular flange 22 extending outwardly from one end and a metal base member 27. Septum 28 and metal base member 27 cooperate to form a sealed plenum chamber, which is depicted as an internal cavity 26 in FIG. 3. Nipple 24 is in fluid communication with internal cavity 26. Flexible conduit 16 is attached to nipple 24 at some point in the procedure, typically after injection port 18 has been implanted. Fluid is added to or removed from interior cavity 26 by inserting a Huber needle percutaneously into silicone septum 28 of injection port 18. Although septum 26 is made of silicon, the means of the injection port for receiving a needle includes any structure configured to self seal after puncture with a non-coring needle.

Although a specific configuration for injection port 18 is disclosed herein, there are many suitable configurations which may be used in conjunction with the present invention.

As shown in FIGS. 2 and 3, injection port 18 includes three integral rotatable circumferentially spaced retention members/fasteners 30, each of which is rotatably carried by a respective pin 32. Each fastener 30 is disposed to rotate in a respective radial plane, about a respective tangential axis. Each pin 32 is supported by a respective fastener support 34 which is carried by flange 22. For each fastener support 34, portion 22a of flange 22 extends generally radially outward, with a pair of spaced apart upright flanges 34a and 34b, defining a gap therebetween, extending upwardly relative to top surface 22b of flange portion 22a, adjacent either side of slot 36. Recesses 36a may be formed into the side of housing 20 if necessary to provide clearance for rotation of rotatable retention members 30. Fastener supports 34 may be of unitary construction with flange 22, or may be mounted thereon in any suitable manner.

Each flange 34a and 34b includes a respective mutually aligned hole into which pin 32 is pressed with an interference fit sufficient to retain pin 32 therein. In the depicted embodiment, ribs 38a and 38b extend from the facing inner surfaces of flanges 34a and 34b, and bear against fasteners 30 to keep them from rotating freely so that fasteners 30 may be kept a non-deployed state until implantation.

Flange 22 includes two circumferentially spaced recesses 40 (only one of which is visible in FIG. 2). Flange 22 includes a stepped/raised portion 22c overlying recess 40. It is noted that recess 40 may be formed in flange 22 without including raised portion 22c.

The teachings of this invention may be practiced with any suitable configuration of a injection port, such as having a smaller flange or a discontinuous flange. Three fasteners 30 are effective to prevent injection port 18 from flipping over after implantation, such as due to passive or induced movements of the patient. However, the present invention is not limited to the use of three fasteners, and one or more fasteners may be used.

Figure 4:
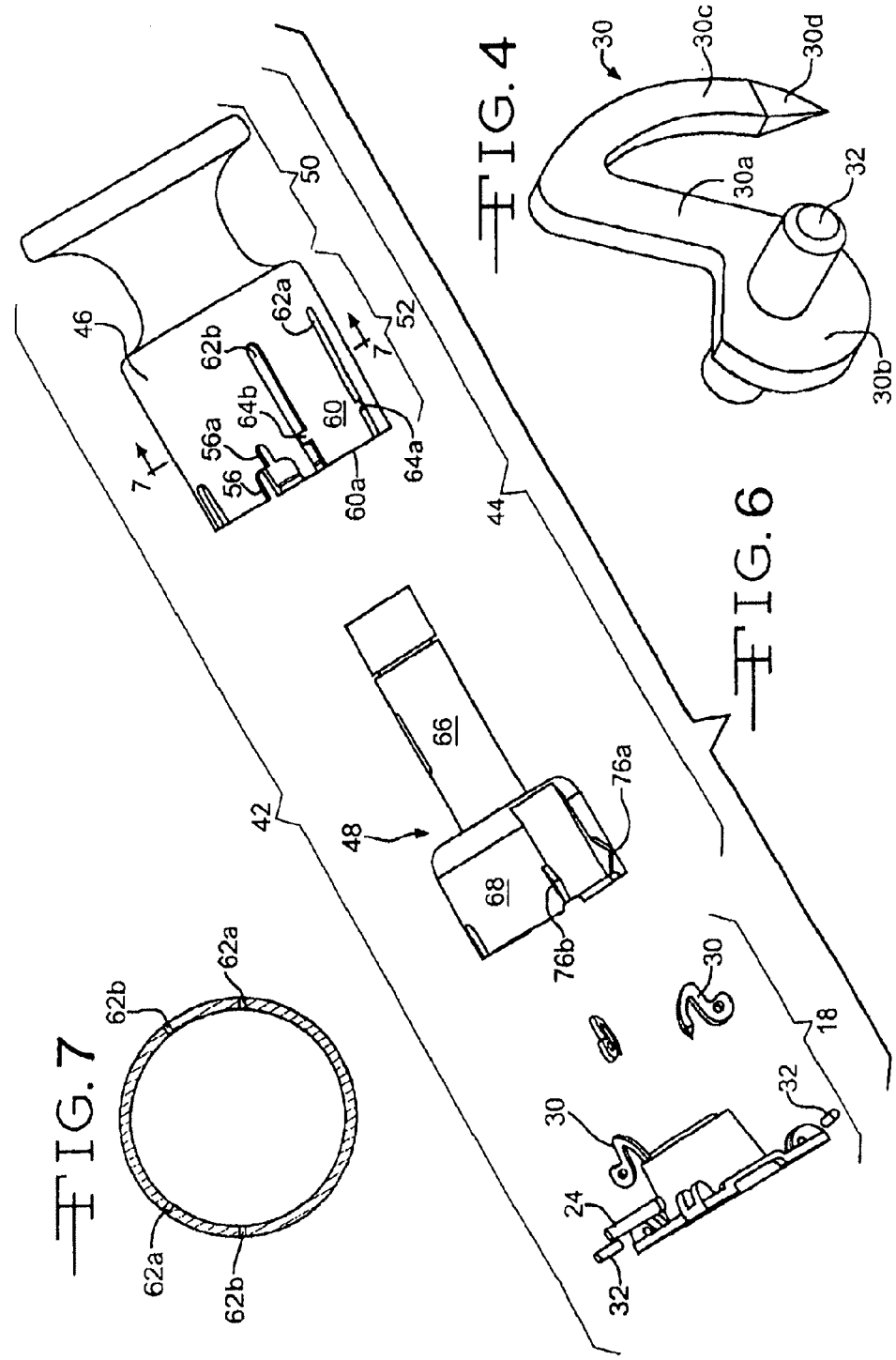
FIG. 4 is a perspective view of the rotatable retention member.

Referring to FIG. 4, rotatable retention member 30 is formed as a hook, having arm 30a extending from base portion 30b to arcuate portion 30c. Arcuate portion 30c terminates in tip 30d which is sharp enough to penetrate tissue.

Figure 5:
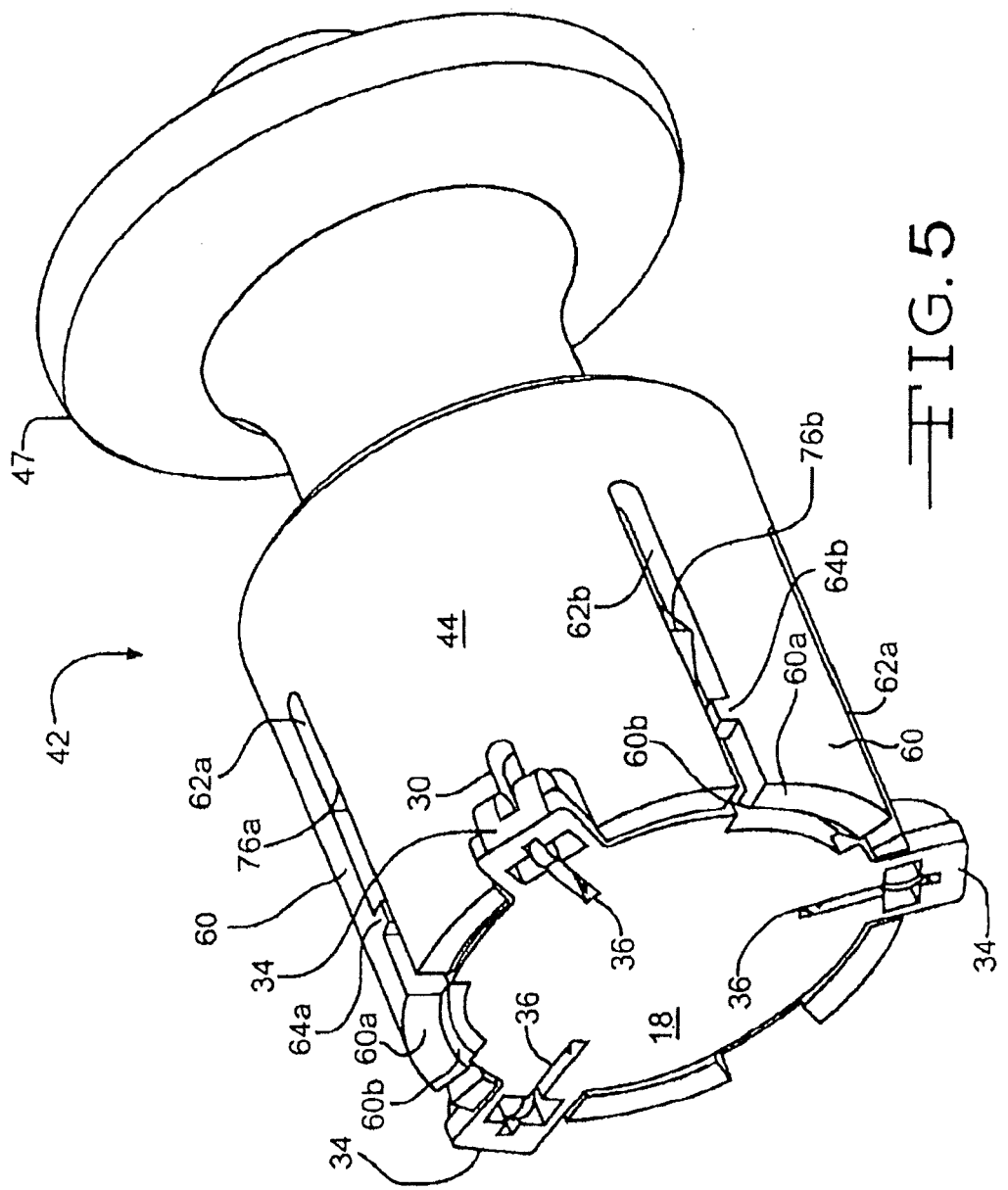
FIG. 5 is perspective view of an injection port attachment assembly with the injection port of FIG. 1 installed in an applicator.

FIGS. 5 and 6 illustrate injection port assembly 42 with injection port 18 installed in applicator subassembly 44. Applicator subassembly 44 includes base 46 and plunger 48.

Figure 8:
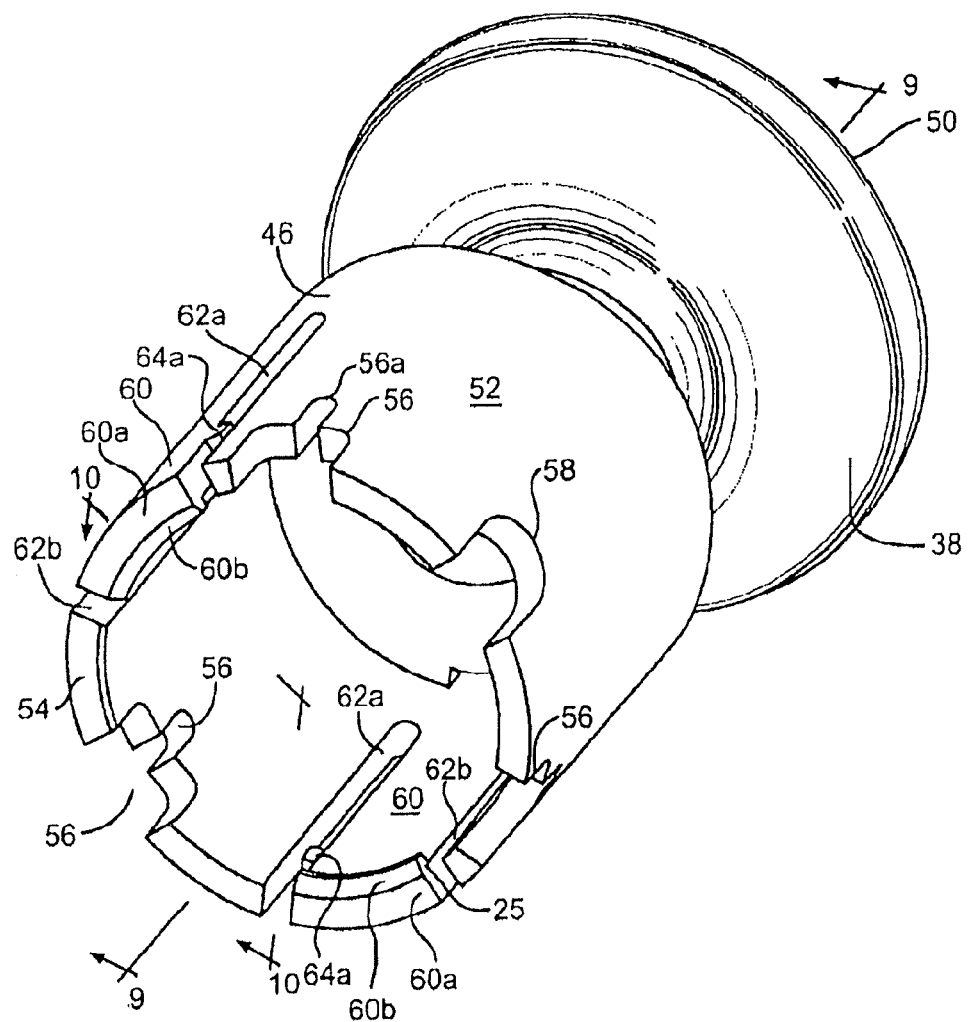
FIG. 8 is a perspective view of the base of the applicator subassembly of FIG. 5.
Figure 9:
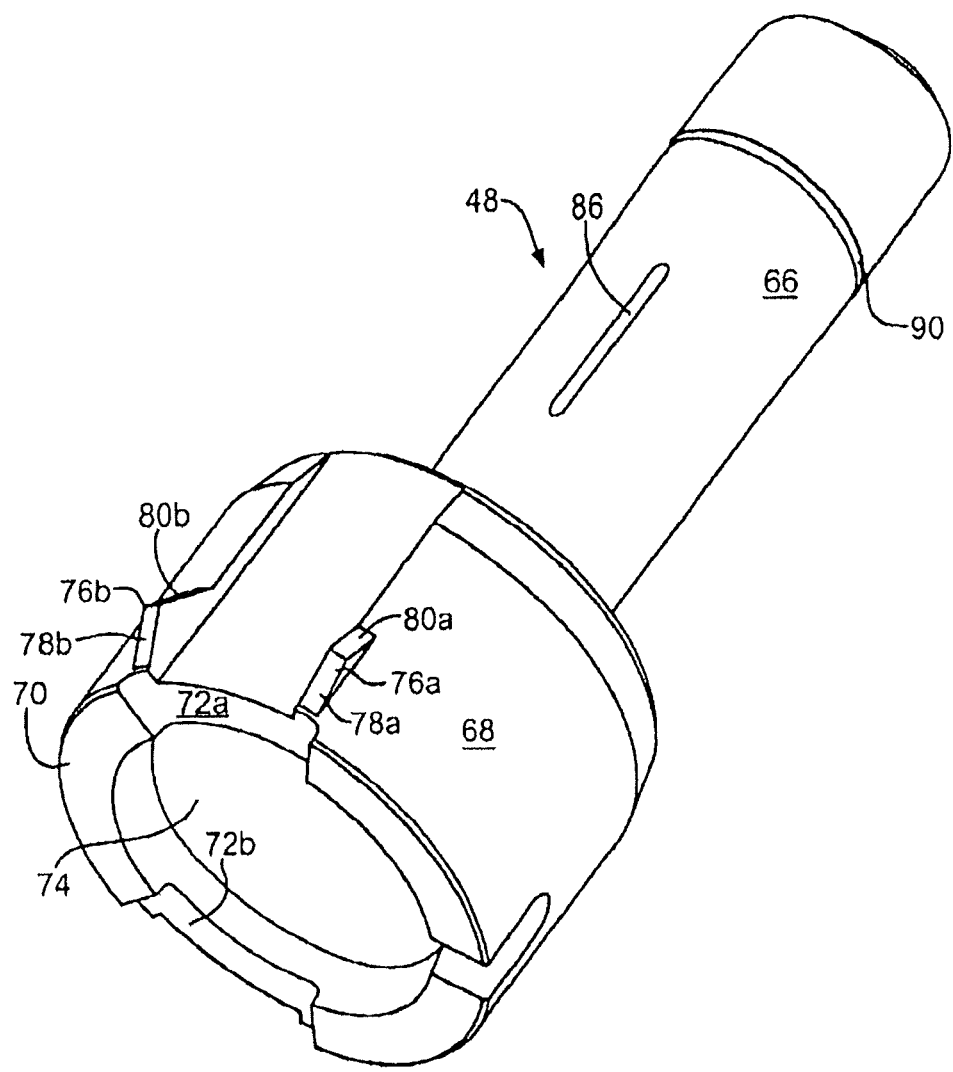
FIG. 9 is a perspective view of the plunger of the applicator subassembly of FIG. 5.

Referring also to FIGS. 7, 8 and 9, base 46 includes handle portion 50, which can be any suitable configuration, and tubular housing portion 52. End 54 includes recesses 56 dimensioned and shaped to receive fastener supports 34 and portions 22a. Each recess includes slot portion 56a which provides clearance for rotatable retention member 30. End 54 also includes recess 58, which provides clearance for nipple 24 when injection port 18 is installed in applicator subassembly 44.

Base 46 includes two circumferentially spaced resilient retention members 60, each defined by two respective elongated slots 62a and 62b. Each pair of slots 62a and 62b are circumferentially spaced a distance such that retention members 60 are essentially cantilevered springs which may be deflected outwardly to release injection port 18, as will be described below. Extending from each longitudinal edge of each retention member 60 near end 60a is a respective retention member actuator 64a and 64b. End 60a includes an inwardly extending lip 60b. The arcuate width, height and depth of recess 40 are complementary to the corresponding dimensions of lip 60b, such that lip 60b engages recess 40 to thereby retain injection port 18 at end 54 of base 42.

As seen in FIG. 6, plunger 48 includes shaft portion 66 and cylindrical portion 68, both of which are shaped and sized complementary to corresponding portions of base 46 so as to be axially moveably received therein. End 70 of cylindrical portion 68 is configured to complementarily engage flange 22, and includes axial recesses 72a and 72b which align with raised portion 22c. End 70 may alternatively be flat, if the configuration of flange 22 dictates. Cylindrical portion 68 defines cavity 74 which is shaped to receive injection port 18 without interfering with the desired engagement between end 70 and flange 22.

Cylindrical portion 68 includes pairs of spaced apart, outwardly extending actuators 76a and 76b. Actuators 76a and 76b are depicted as ramps, having inclined leading surfaces 78a and 78b and declined trailing surfaces 80 and 80b. When plunger 48 is disposed within base 46, each actuator 76a and 76b is disposed within a respective slot 62a and 62b. As will be described below, as plunger is depressed to advance end 70 toward end 54, actuators 76a and 76b engage respective resilient member actuators 64a and 64b and urge them outwardly, causing resilient members 60 to move outwardly, and eventually moving lips 60b out of respective recesses 22c, releasing injection port 18 from applicator subassembly 44.

Figure 10:
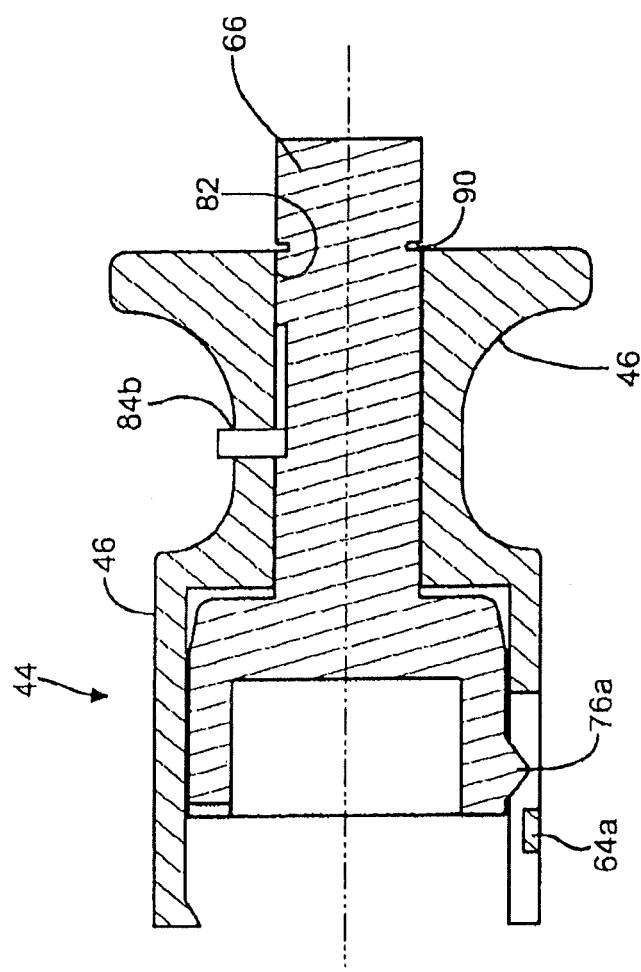
FIG. 10 is a cross sectional view of the applicator subassembly of FIG. 5, taken at the same location as indicated by line 10-10 of FIG. 8.

FIG. 10 illustrates applicator subassembly 44 in cross section. Base 46 includes bore 82 into which shaft portion 66 is slidably disposed. Plunger 48 is retained in base 46 by pin 84 which is secured to base 46, and extends into longitudinal slot 86 in shaft portion 66.

Figure 11:
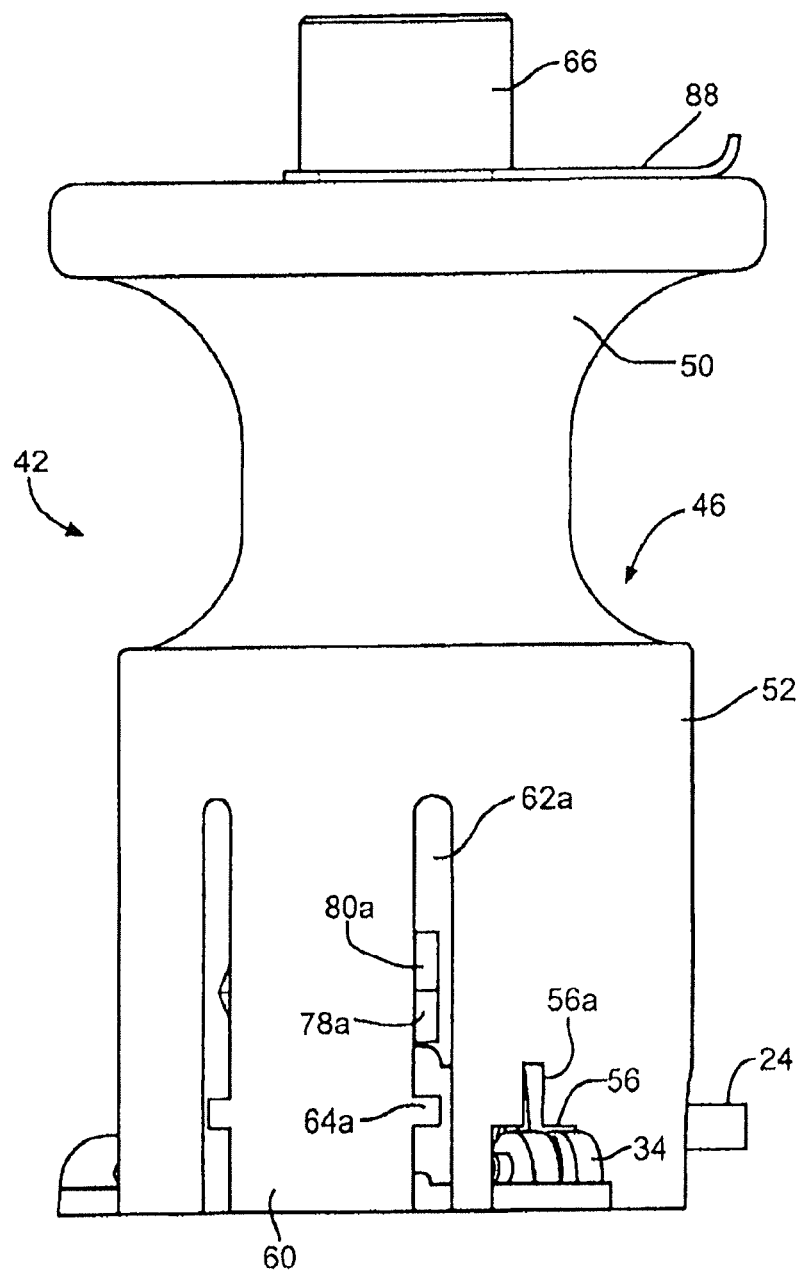
FIG. 11 is a side view of the injection port attachment assembly shown in FIG. 5 prior to implantation.
Figure 12:
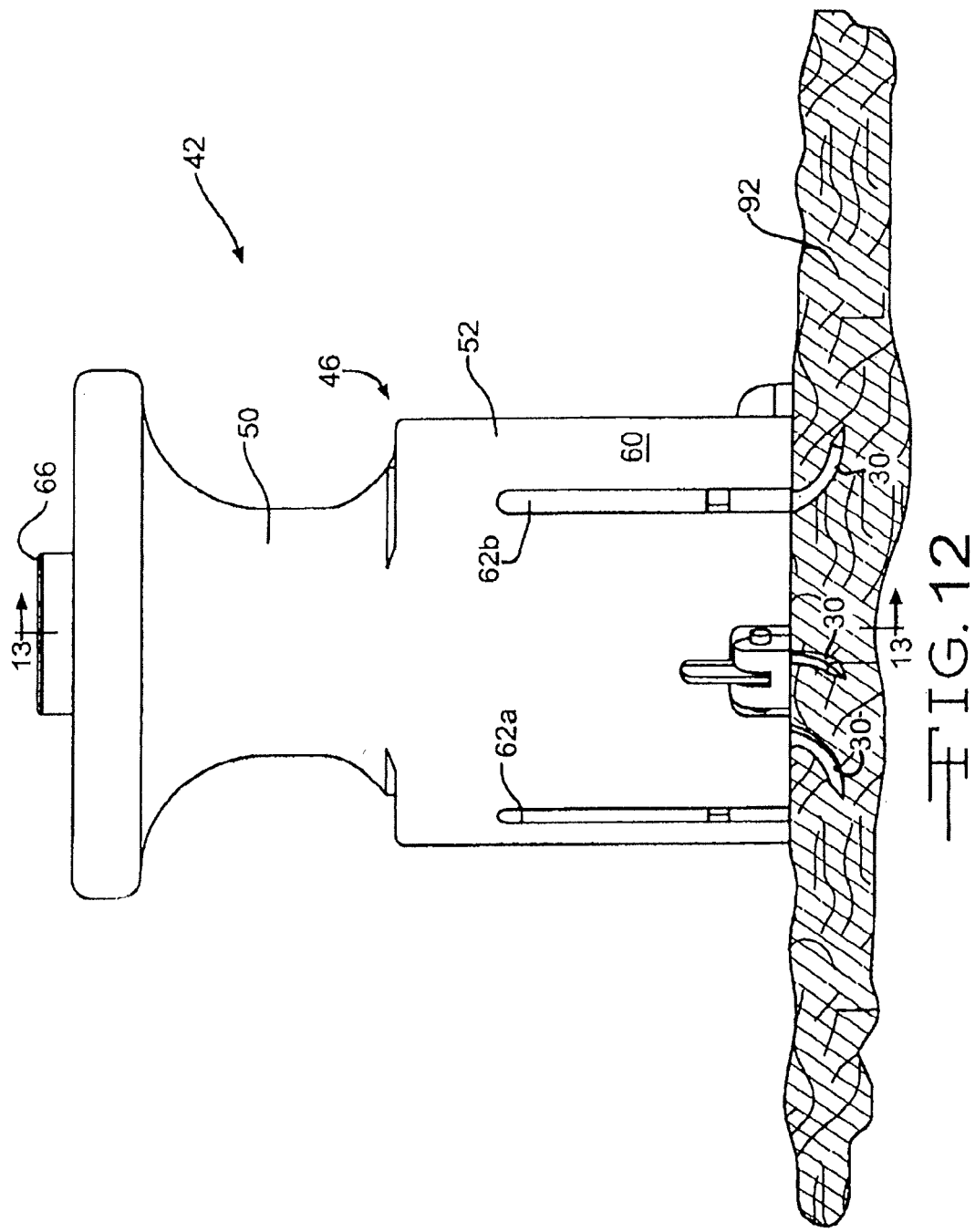
FIG. 12 is a side view of the injection port attachment assembly shown in FIG. 5 following implantation prior to release of the injection port from the applicator subassembly.

Referring to FIGS. 5 and 11, injection port assembly 42 is illustrated, having injection port 18 installed in applicator subassembly 44. Fasteners 30 are in the retracted position in an undeployed state. End 66a of shaft 66 extends out of handle portion 50 as shown. To assemble injection port 18 into applicator assembly 44, fastener supports 34 are aligned with openings 56, and snapped into place with lips 60b engaging recesses 22c. To keep plunger 48 in place, lock clip 88 engages annular groove 90 in shaft portion 66. To implant injection port 18, clip 88 is removed and shaft portion 66 is advanced through bore 82, contacting fasteners 30 and rotating them into the deployed state at a position piercing and engaging fascia layer 92, as shown in FIG. 12. Further advancement of shaft portion 66 will disengage injection port 18 from applicator subassembly 48, as described below.

Figure 13:
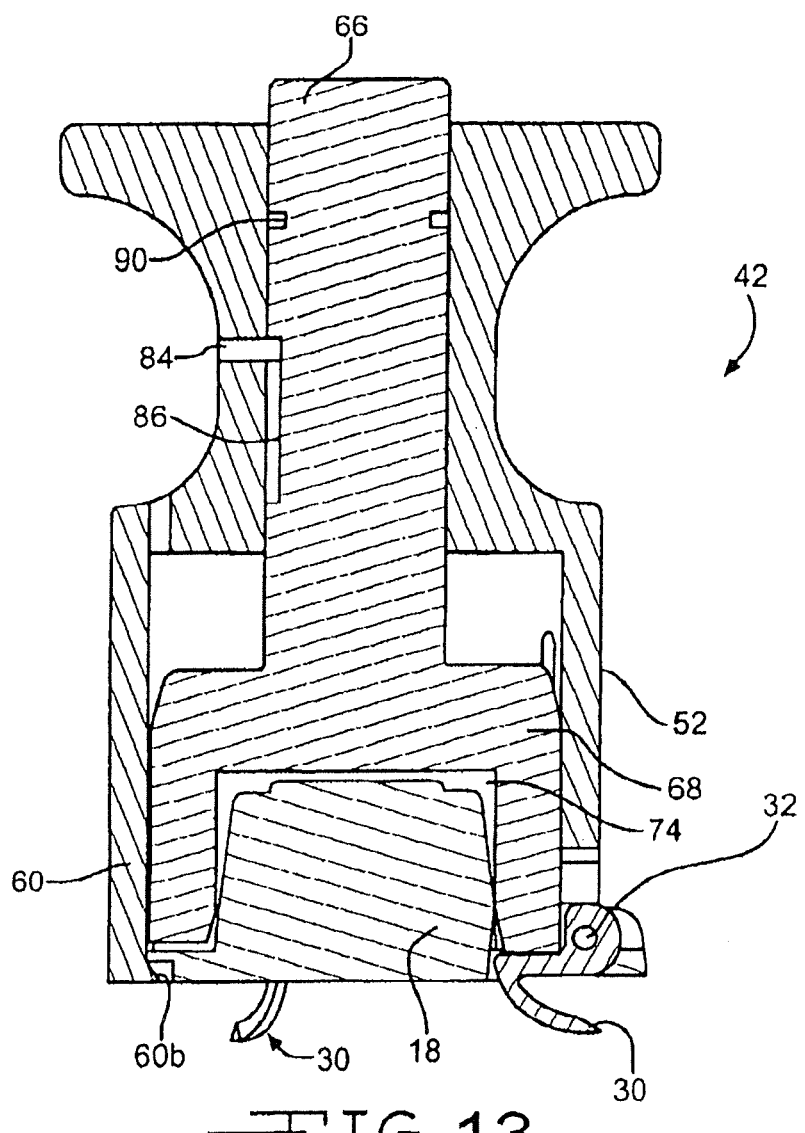
FIG. 13 is a cross sectional view of the injection port attachment assembly taken along line 13-13 of FIG. 12.

FIG. 13 is a cross sectional view of the injection port attachment assembly taken along line 13-13 of FIG. 12. At this position, end 70 has rotated rotatable retention members/fasteners 30 about 90° from their retracted position in an undeployed state, by initially contacting fasteners 30 at their uppermost point in the retracted position. This creates a moment about pin 32, rotating fasteners 30, and transmitting sufficient force thereto to pierce the fascia layer. Full rotation of fasteners 30 into the deployed state is shown in FIG. 13, although at this position end 70 has not bottomed against the upper surface of flange 22.

Figure 14:
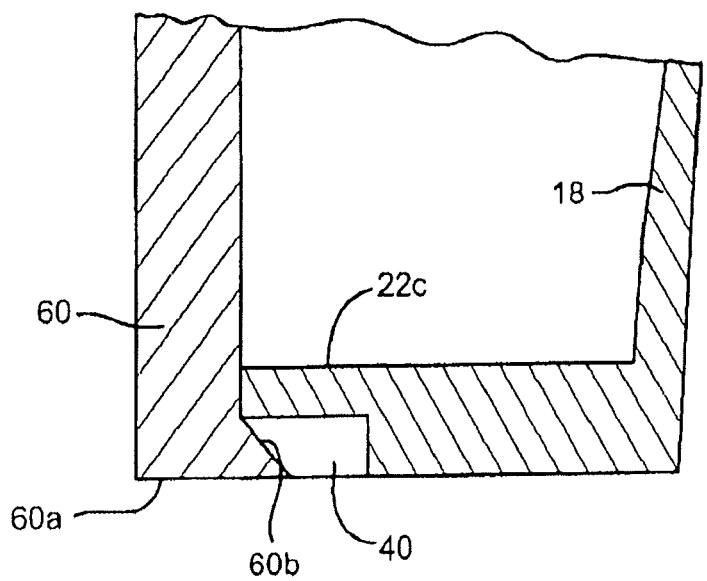
FIG. 14 is an enlarged portion of FIG. 13 showing a fragmentary cross sectional view of the resilient retention member and injection port.
Figure 15:
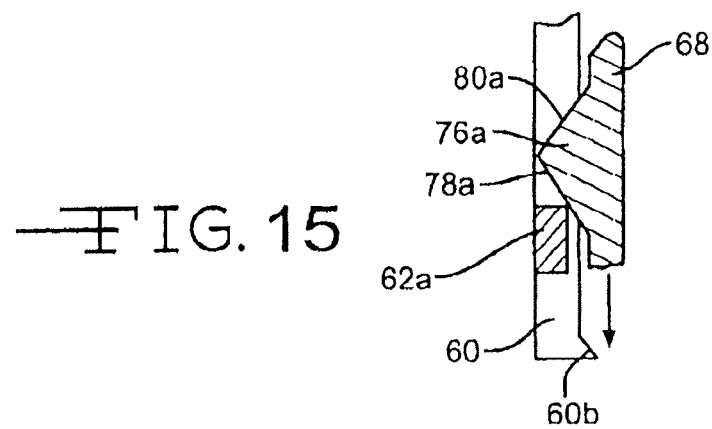
FIG. 15 is an enlarged, fragmentary view showing the position of the actuator ramp and the resilient retention member actuator.

Referring also to FIG. 14, which is an enlarged illustration of a portion of FIG. 13, showing resilient retention member 60 still maintaining lip 60b in recess 40. Also referring to FIG. 15, at the position illustrated in FIG. 13, ramp actuators 76a and 76b are in contact with retention member actuators 62a and 62b (62b and 76b are not shown in FIG. 15). Longitudinal advancement of plunger 66 causes retention member actuators 62a and 62b to ride up ramps 78a and 78b, urging resilient retention members 60 outwardly. As plunger 66 advances, portions of end 70 engage flange 22, and begin urging injection port 18 axially out. When ramps 78a and 78b have moved retention members 60 outwardly enough, lips 60b move out of recesses 40 and injection port 18 is released. Further travel of plunger 66 pushes flange 22 past end 54 of housing 52. Slot 86 bottoms against pin 84, preventing further travel of plunger 66.

Figure 16:
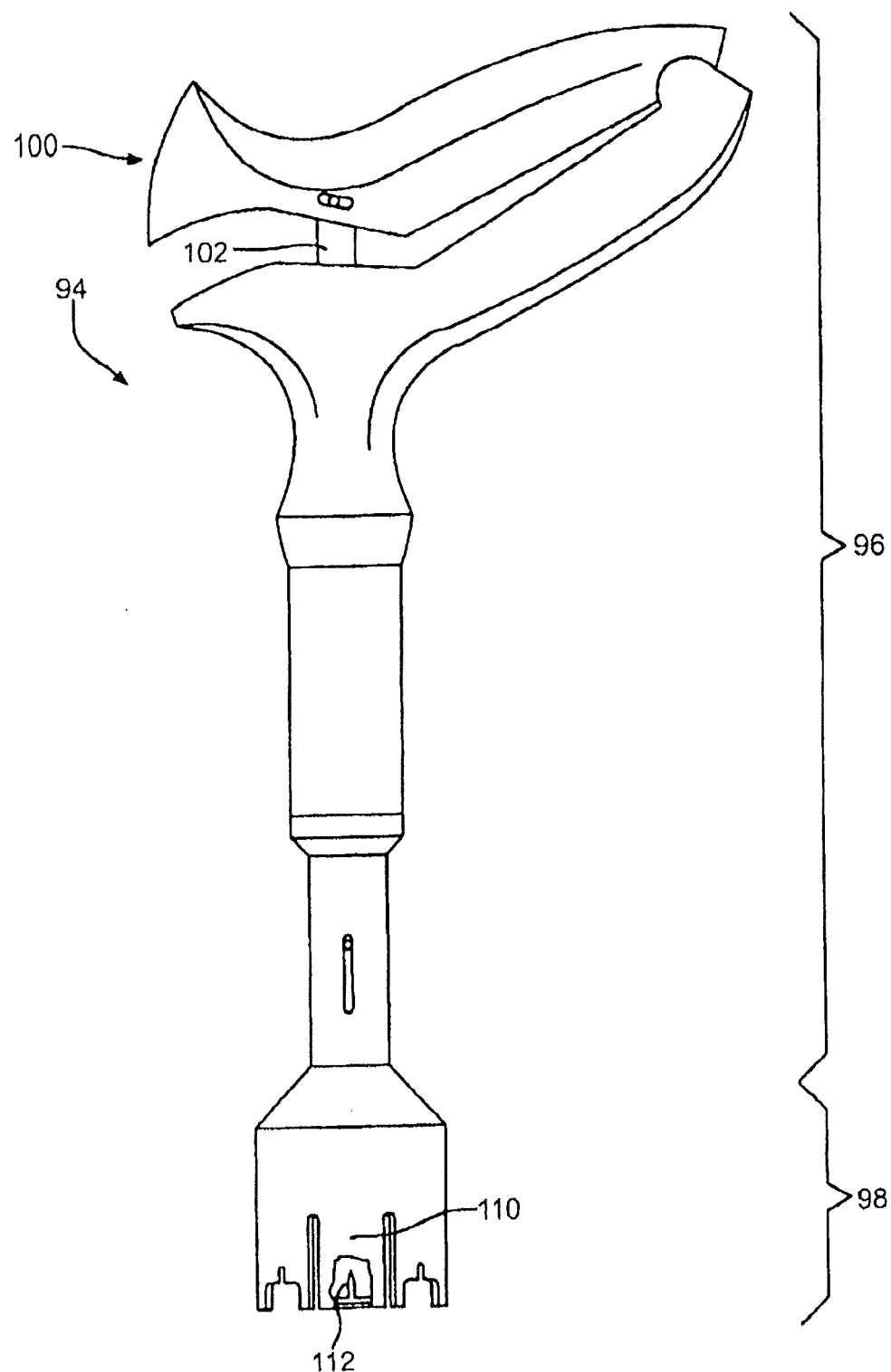
FIG. 16 is a side view of an alternate embodiment of an injection port attachment assembly according to the present invention.
Figure 18:
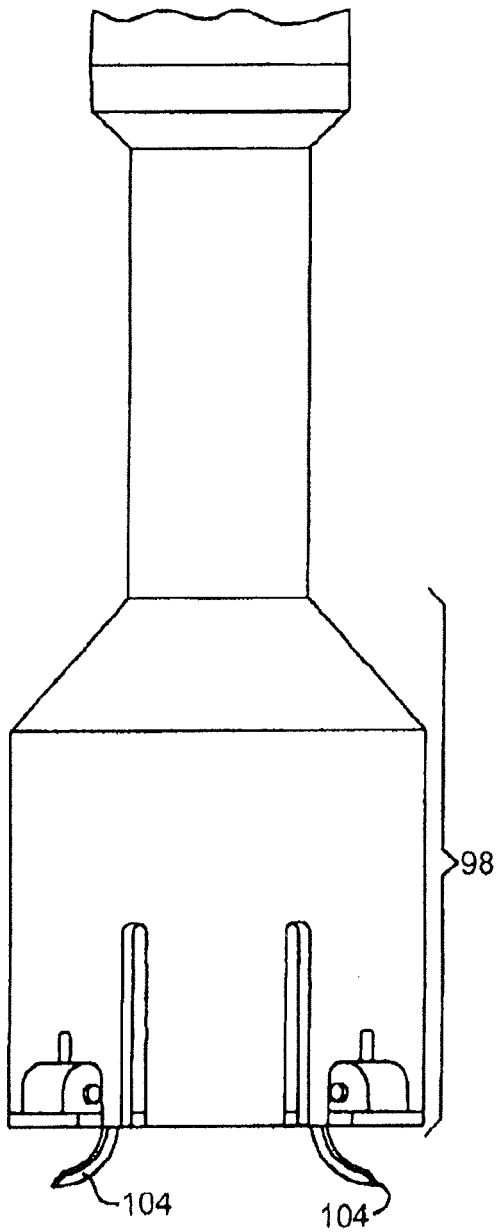
FIG. 18 is a fragmentary side view of the attachment end of the injection port attachment assembly shown in FIG. 16.

FIG. 16 is a side view of an alternate embodiment of an injection port attachment assembly according the present invention. Injection port attachment assembly 94 includes handle portion 96 which is rotatable relative to cylindrical portion 98. Handle portion 96 includes grip 100 connected to shaft 102. In addition to the configuration of handle portion, injection port attachment assembly 94 differs from 42 injection port attachment assembly 94 in that it has four equally circumferentially spaced rotatable retention members 104 (see FIG. 18), and in the configuration of the retention member actuators and the actuator ramp.

Figure 17:
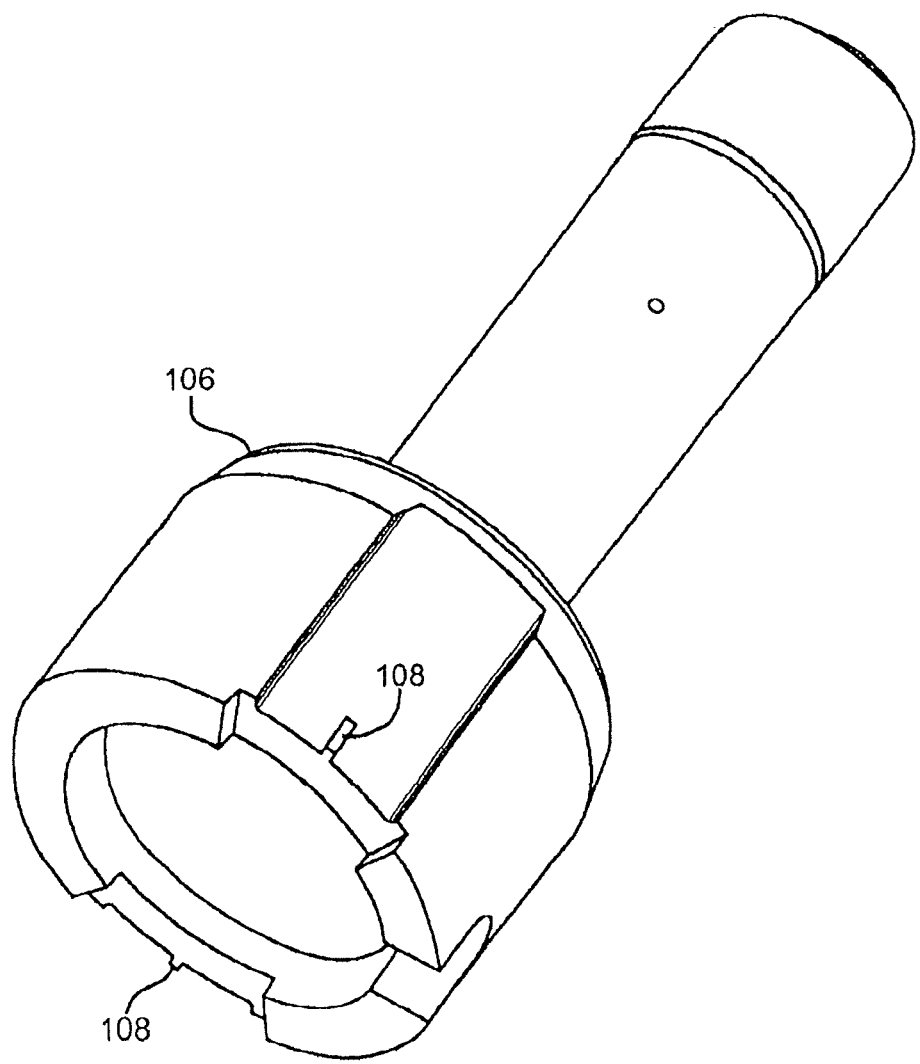
FIG. 17 is a perspective view of the plunger of the applicator subassembly of FIG. 16.
Figure 19:
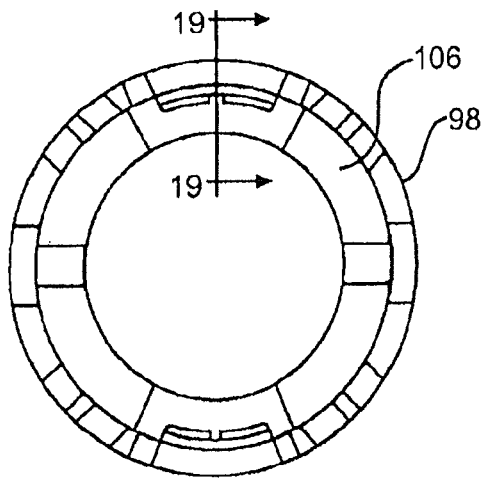
FIG. 19 is en end view of the applicator subassembly of FIG. 16.
Figure 20:
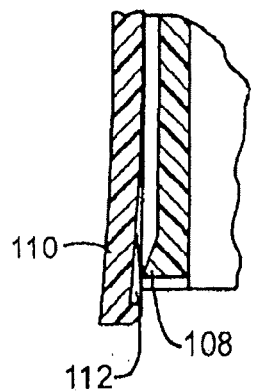
FIG. 20 is an enlarged, fragmentary cross sectional view of the attachment end of the applicator subassembly of FIG. 16.

Referring to FIG. 17, plunger 106 includes two diametrically opposite resilient retention member actuators 108. Resilient retention members 110 are disposed diametrically opposite each other since there are four rotatable retention members 104. If only three retention members were present, resilient retention members would be disposed as described above. Referring to FIG. 20, resilient retention member 110 includes ramp actuator 112. As plunger 106 is advanced, actuator 108 engages ramp 112, urging resilient retention members 110 outwardly and out of engagement with the injection port.

It is noted that in the embodiment depicted in FIGS. 16-20, plunger 106 bottoms out, after disengaging resilient retention members, without pushing the injection port out. Either embodiment described so far may be configured to push or not to push the injection port out at the end of the plunger stroke.

Figure 21:
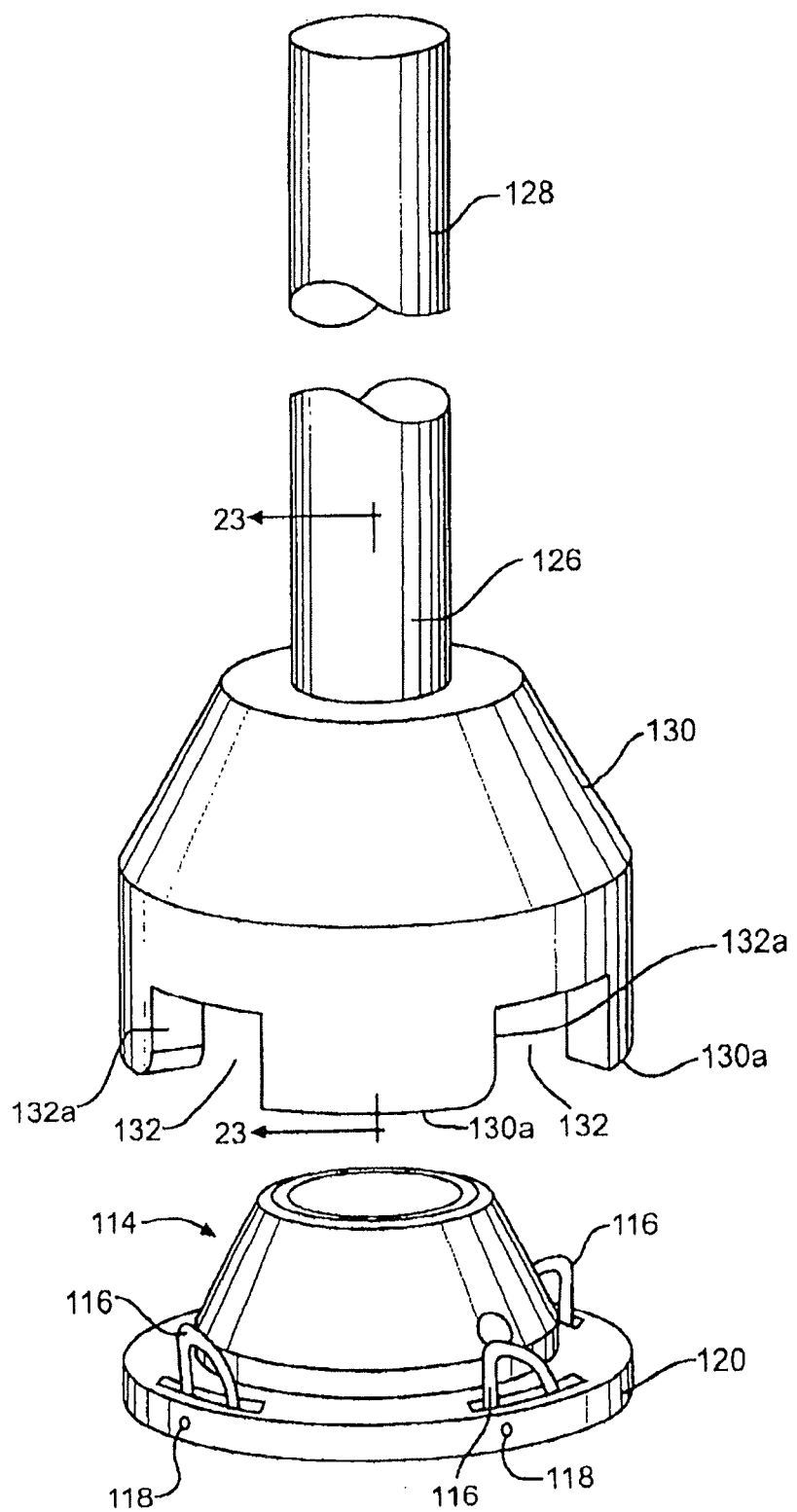
FIG. 21 is a perspective view of an alternate embodiment of a self attaching injection port in accordance with the present invention and an applicator configured for use therewith.

Referring to FIG. 21, there is shown another embodiment of a injection port constructed in accordance with the present invention. In this embodiment, injection port 114 includes a plurality of rotatable retention members/fasteners 116, each disposed to rotate in a tangential plane. Rotatable fasteners 116 are rotatably carried by respective pins 118 which are pressed radially into flange 120.

Figure 22:
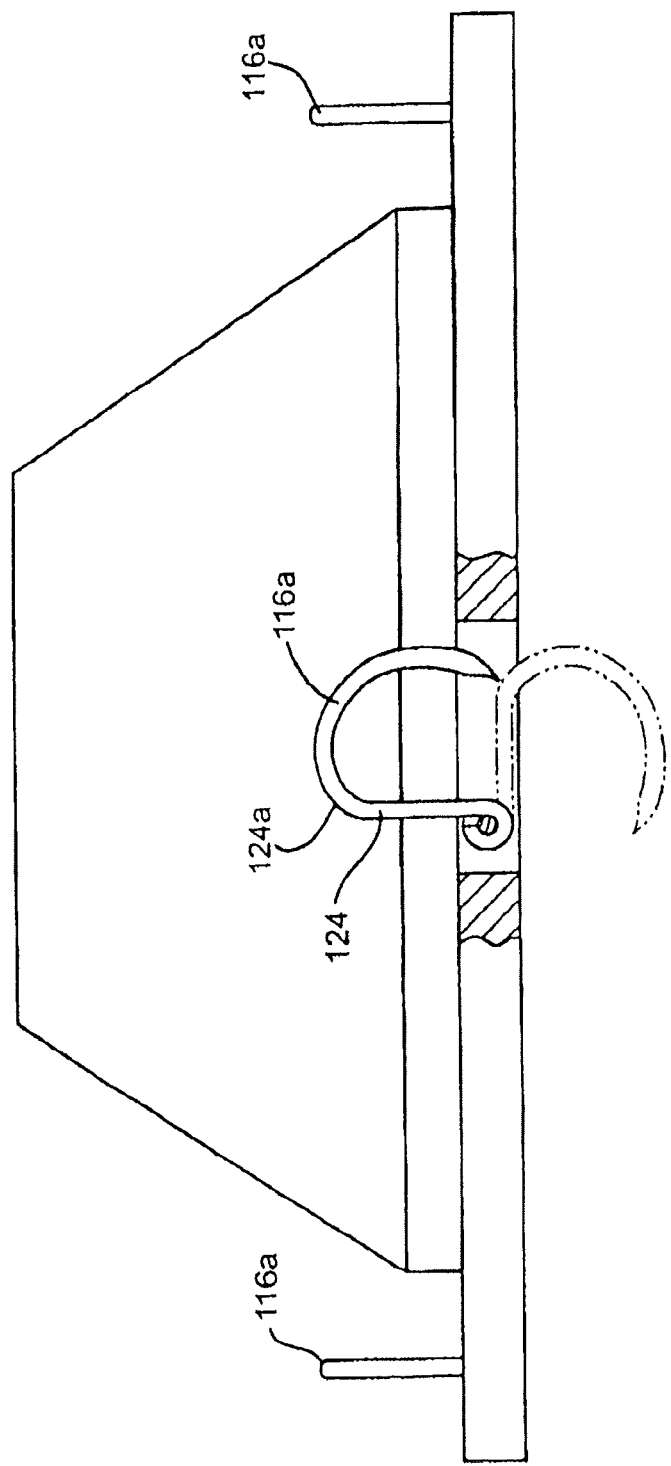
FIG. 22 is an enlarged side view of the injection port of FIG. 21 with a portion cut away to show a rotatable retention member.
Figure 23:
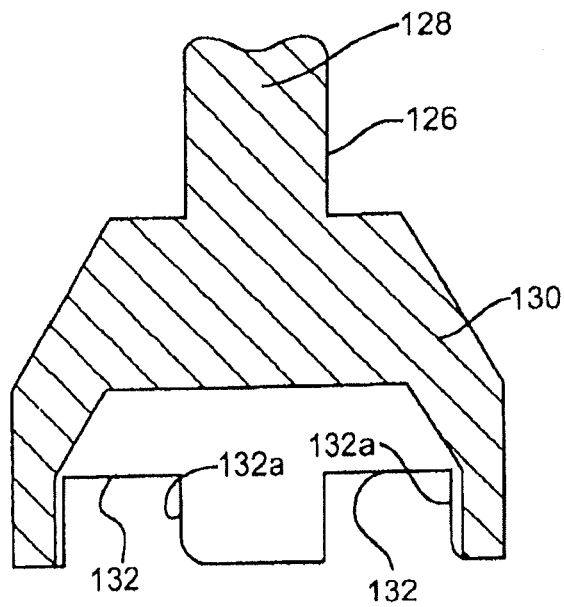
FIG. 23 is a fragmentary, cross sectional view of the applicator taken along line 23-23 of FIG. 21.

Referring also to FIG. 22, an additional configuration of rotatable retention members/fasteners 116a. Fastener 116a has a generally circular cross section, and includes a generally arcuate portion 122 which extends higher than end 124a of arm 124 is shown. Operation of fasteners 116 and 116a is the same.

As seen in FIGS. 21 and 22, applicator 126 includes shaft 128 and cylindrical end 130. Cavity 132 forms the center of cylindrical end 130, providing clearance for injection port 114. Cylindrical end 130 includes circumferentially spaced openings 132 which are sized and spaced to align with rotatable retention members 116.

Figure 24:
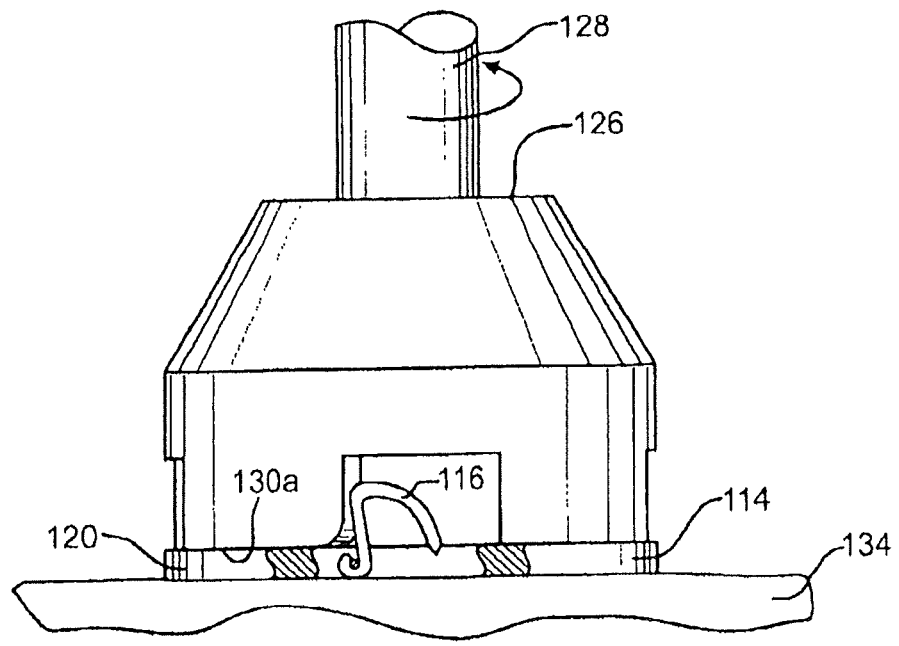
FIG. 24 is a side view of the injection port attachment and applicator of FIG. 21 prior to implantation, with a portion cut away to show a rotatable retention member.
Figure 25:
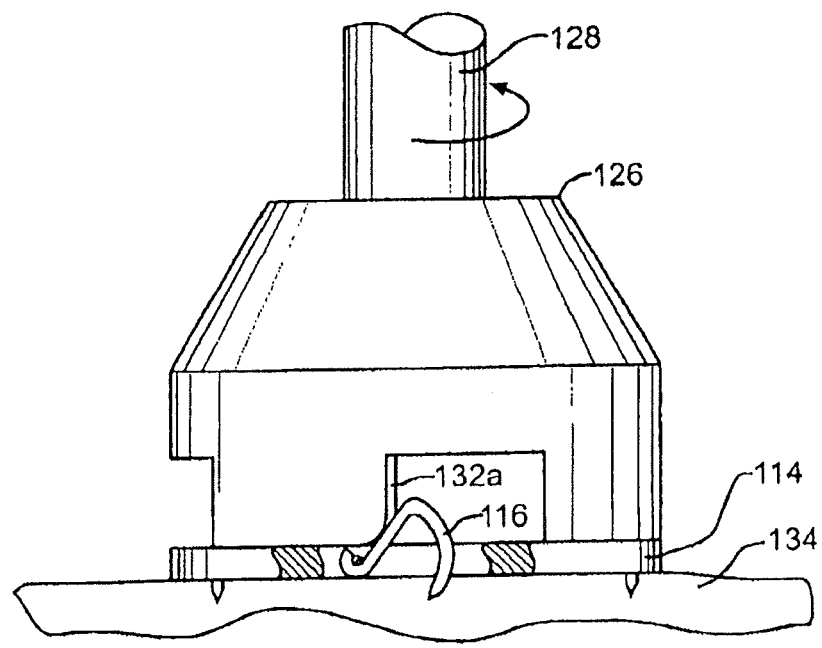
FIG. 25 is a side view similar to FIG. 24, with the applicator slightly rotated showing initiation of implantation.
Figure 26:
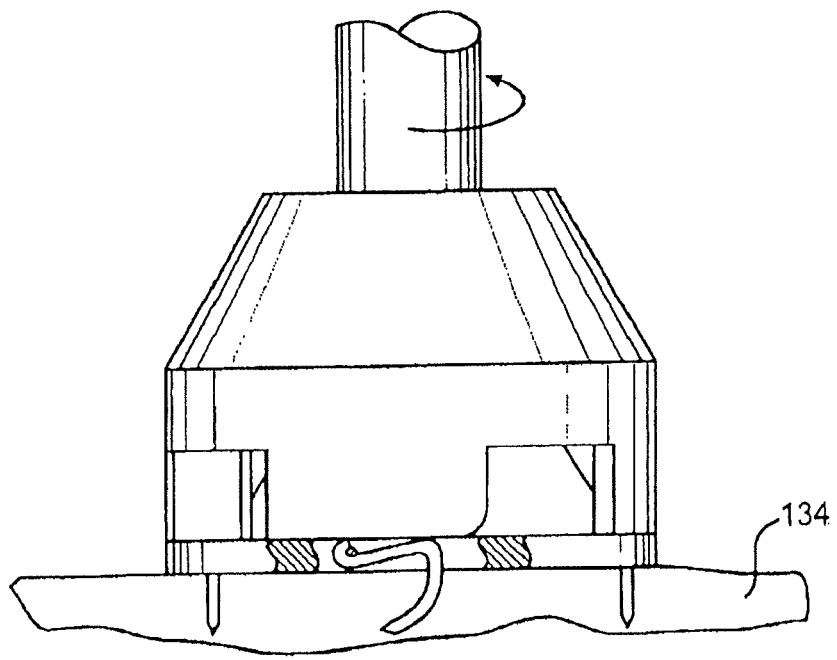
FIG. 26 is a side view similar to FIG. 25, with the applicator rotated further showing completion of implantation.
Figure 30:
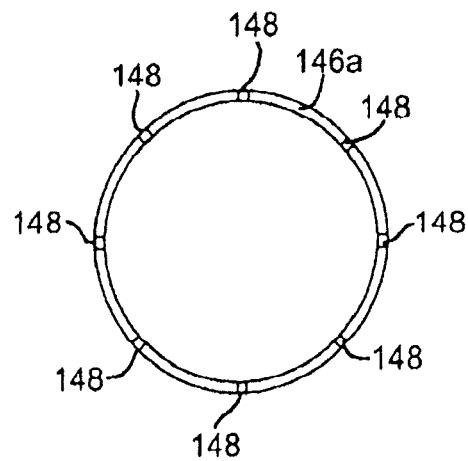
FIG. 30 is an end view of the applier of FIG. 28.
Figure 31:
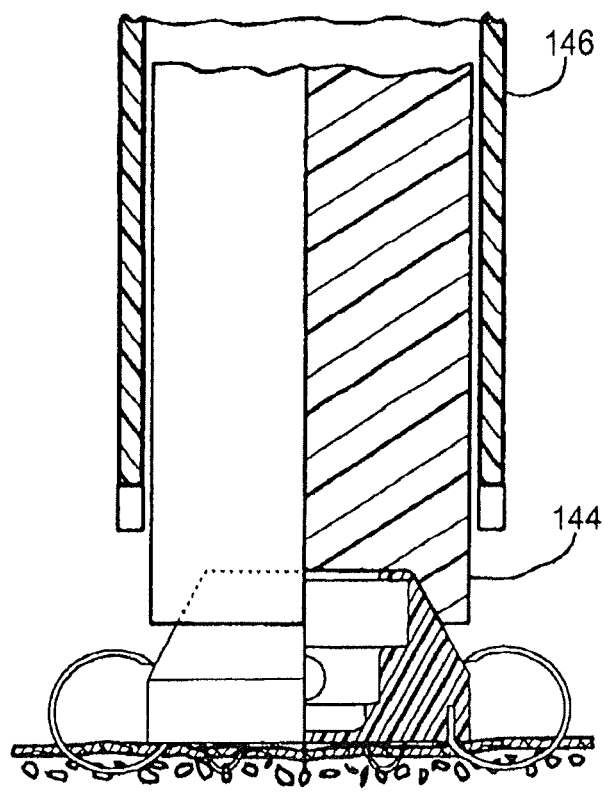
FIG. 31 illustrates the withdrawal and shows the injection port and applier of FIG. 30 during implantation.

Referring to FIGS. 24, 25 and 26, injection port 114 is implanted by placing it on fascia layer 134 with fasteners 116 in the retracted position in an undeployed state. End 130a of applicator 126 is placed in contact with flange 120, with openings 132 aligned with fasteners 116. With sufficient axial force, shaft 128 is rotated, urging edges 132a against fasteners 116, causing them to rotate and pierce fascia layer 134. Edges 132a include rounded portions where they transition to end 130a for smooth engagement with fasteners 116. As seen in FIG. 26, injection port 114 is implanted when recesses 132 of applicator 126 have been rotated into the deployed state at the position as shown.

Referring to FIG. 27, there is shown another embodiment of an injection port with integral, moveable fasteners. Injection port 136 includes eight circumferentially spaced fasteners 138 extending radially outward (four shown in FIG. 27). This embodiment of the present invention is not limited to the use of eight fasteners, and one or more fasteners may be used. Fasteners 138 extend from and are secured to bottom surface 136a of the distal end of injection port 136 in any suitable manner, such as by one end 138a being pressed, welded, epoxied, or otherwise secured into a blind hole formed in bottom surface 136a. Distal end 138b are sharp for tissue penetration.

As depicted, in the undeformed deployed state, each fastener 138 is a single coil, forming a hook shape, with distal end 138b disposed touching or otherwise adjacent the side of housing 140 of injection port 136. It is noted that the relative positions of the side of housing 140 and distal ends 138b may leave fasteners 138 in a somewhat deformed state with some stress and strain. Fasteners 138, also referred to as radial elements, are flexible, being made of any suitable material. Material having super elastic properties, such as a nickel titanium alloy, for example Nitinol® wire.

Fasteners 138 may be of any suitable dimensions. In one example, Nitinol® wire having a diameter in the range of 0.020-0.080 mm, coiled to a diameter of about 4-8 mm was used.

Referring also to FIGS. 28-31, implantation of injection port 136 may be accomplished through use of applier 142. Applier 142 includes plunger 144 axially reciprocable disposed inside of tube 146. End 144a is shaped complementarily to housing 140 of plunger 144. End 146a of tube 146 includes a plurality of circumferentially spaced slots 148 located complementarily to the spacing of fasteners 138. Tube 146 may include a slot to accommodate the nipple extending from injection port 136.

As seen in FIG. 28, injection port 44 is initially disposed inside of tube 146, spaced up from end 146a a distance sufficient to orient fasteners 138 in an undeployed state at a position such that tips 138b are respectively disposed in slots 148 without extending outside of the diameter of tube 146. The wall thickness of tube 146 at end 146a is sufficient to provide adequate length for tips 138b to remain disposed therein without extending beyond the outer diameter of tube 146. Tube 146 may be uniform along its entire length, or have a thin wall along its length with a thicker wall suction at end 146a, such as provided by a collar (not illustrated) disposed about end 146a, to provide the desired radial thickness for slots 148.

Although FIG. 28 illustrates flexible fasteners 138 as extending straight between slots 148 and bottom surface 136a, fasteners 138 may assume a curved configuration dictated by their specific physical properties and the distance between slots 148 and bottom surface 136a. Slots 148a are configured to keep fasteners 138 in a suitable orientation and configuration to feed through slots 148 as described below. Tube 146 may be made of any suitable material, such as stainless steel or plastic.

Injection port 136 may be releasably held in the appropriate location within tube 146 in any suitable manner. For example, a pin may extend through a hole in tube 146 to restrain injection port 136 across bottom 1364a until implantation; an adequate frictional fit between injection port 136 and the inside of tube 146 may be provided, with the tightest fit being at the highest location of injection port 136 within tube 146; end 144a could be configured to releasably engage injection port 44, with plunger 144 being retained in tube 146.

It is contemplated, but not required, that applier 142 will be provided to the surgeon with injection port 136 premounted inside of tube 144 as a sterilized assembly. Implantation of self attaching injection port 136 is accomplished by urging end 146a against fascia layer 150 to depress the tissue surface slightly thereby upraising the tissue so that fasteners 138 may go through it. The surgeon then pushers plunger 144 to deploy fasteners 138, and withdraws tube 146. Sharp tips 138b penetrate through and curl back out of fascia layer 150, and stop against the side of housing 140 to protect tips 138b. In the deployed state, fasteners 138 are in a "relaxed" configuration, having less deformation, and therefore less stress strain, than in the pre-attachment, deformed state.

Deformable fasteners 138 may be sized to provide holding strength similar to sutures, with the flexibility of fasteners 138 allowing injection port 136 to be removed without the tissue being ripped. For example, after attachment, injection port may be reposition by grasping injection port 136 and pulling it up, uncurling fasteners 138 in the process. It may then be reinserted into applier 142 and reimplanted. Applier 142 may also be used to remove injection port 136, such as by configuring end 150a to engage injection port 136 to be withdrawn, as tube 146 is urged against tissue. In such a case, it may be advantageous to provide structure to index plunger 144 relative to injection port 136 and slots 148.

Although flexible fasteners 138 are illustrated extending from bottom 136a, this aspect of the present invention may be practiced with fasteners 146 extending in other directions from injection port 136, such as from the side. As will be appreciated, modifications to applier 142, such as a larger diameter to accommodate the circumferential attachment to injection port 136 for implantation, may be made. It is noted that with flexible fasteners 138 extending from bottom 136a, tips 138a are oriented in a downward pointing undeployed state at a position ready to penetrate the tissue from the top, which allows a smaller diameter than would fasteners extending outwardly from the side. A small diameter applier minimizes the size of the incision, and requires less dissection.

Figure 32:
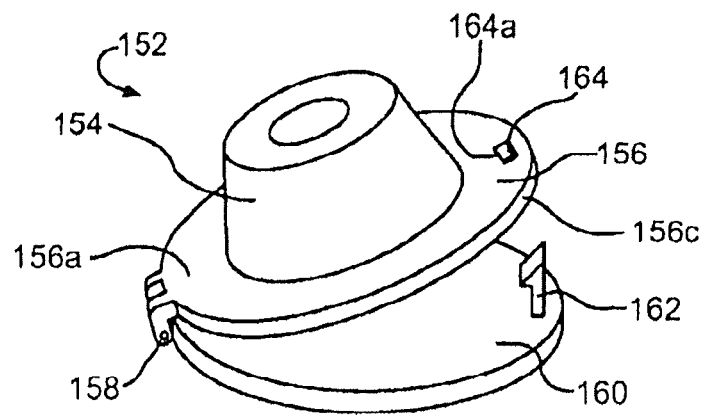
FIG. 32 is a perspective view of another embodiment of an injection port with an integral moveable retention member.

Referring to FIG. 32, another embodiment of an injection port having an integral moveable retention member is illustrated. Injection port 152 includes housing 154 with annular flange 156 extending outwardly from the lower distal end of housing 154. Annular flange 156 includes upper surface 156a and lower surface 156b.

Hinge 158 is carried by annular flange 156, moveably connecting retention member/fastener 160 to flange 156. Hinge 158 may be any structure which allows the necessary relative movement between retention member/fastener 160 and flange 156.

Figure 33:
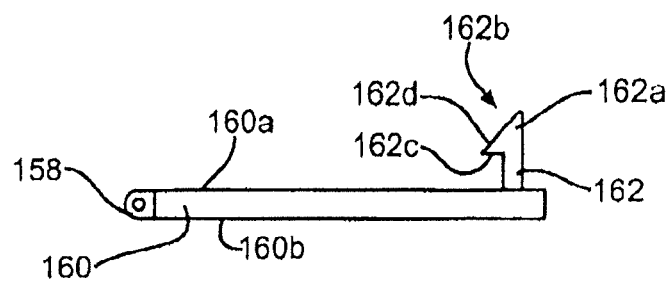
FIG. 33 is a fragmentary side view of the retention member of the injection port of FIG. 32.

Referring also to FIG. 33, retention member 160 includes upper surface 160 and lower surface 160b. Locking member 162 extends upwardly from upper surface 160a, and includes distal tip 162a which is configured to pierce tissue. Locking member 162 also includes locking configuration 162b which is configured to engage annular flange 156 and lock retention member 160 in a deployed state, as described below. As depicted, locking configuration 162b includes step 162c and inclined surface/ramp 162d.

In the embodiment depicted, flange 156 includes opening 164 which is shaped complementary to locking member 162, configured to receive locking member 162 and engage step 162c to maintain locking member 162 and retention member/fastener 160 in the deployed state. Locking member 162 has enough flexibility to allow outward movement of locking member 162 as inclined surface 162d engages and advances along corresponding edge 164a of opening 164. Once locking member 162 has been inserted far enough into opening 164 for ramp 162d to disengage with corresponding edge 164a, step 162c will clear upper surface 156a, and the locking member 162 will move inwardly, with step 162c engaging upper surface 156a to resist withdrawal of locking member 162 from opening 164.

Alternatively, opening 164 may open to outer edge 156c of flange 156, or may even be eliminated, with locking member 162 disposed such that inclined surface 162d engages and advances along outer edge 156c.

Locking member 162 may be made of any suitable material which provides the necessary flexibility, including plastic. Locking member 162 is not limited to the shape shown, and may be of any shape which is functional to retain retention member 162 at the position shown in the deployed state. Locking member 162 and flange 156 may be configured such that distal tip 162a does not extend above, or as far above, upper surface 154a. For example, locking member 162 could include a stop surface which engages the annular flange 156 so as to limit the position of distal tip 162a relative to upper surface 156a.

Retention member 160 may also be made of any suitable material, including plastic.

FIG. 32 illustrates retention member 160, in the undeployed state. Hinge 158 may include a detent to hold retention member 160 in a particular undeployed state position relative to housing 154. To implant injection port 152, retention member 160 is inserted below the fascia tissue, with injection port 152 remaining there above. If necessary, an incision may be made in the tissue sufficient to insert retention member 160. Retention member 160 is moved relative to housing 154 and flange 156 into a deployed state, with distal tip 162a piercing the tissue and engaging opening 164, as illustrated in FIG. 34.

Figure 34:
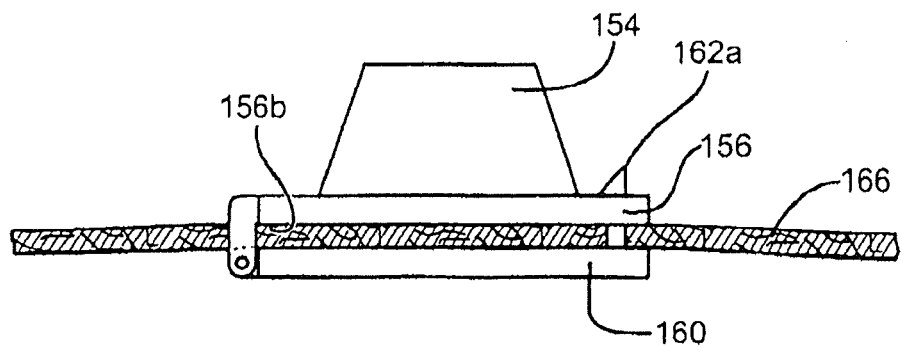
FIG. 34 is a side view of the injection port of FIG. 32, with the retention member in the deployed position; and Reference will now be made in detail to the present preferred embodiment of the invention, an example of which is illustrated in the accompanying drawings.

FIG. 34 illustrates injection port 152 fastened in place, with tissue 166 disposed between flange 156 and retention member/fastener 160. As can be seen in FIG. 34, hinge 158 is located so as to maintain flange 156 and retention member 160 in a spaced apart relationship, creating a gap therebetween within which tissue 166 may be captured. Alternatively, it may be possible to omit the gap if either flange 156 or retention member 160 is flexible enough to so capture tissue 166 without damage.

Although retention member/fastener 160 is illustrated as shaped complementary to flange 156, retention member/fastener 160 does not have to have the same shape as flange 156. For example, retention member/fastener 160 could be a strap. Additionally, housing 154 does not have to include flange 156. Flange 156 could be omitted, with hinge 158 being connected directly to an edge of the distal end of housing 154. The axis of rotation of retention member 160 could be oriented vertically with respect to housing 154 and lower surface 156b of housing 154.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The one or more embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An apparatus, comprising:
    (a) a body sized and configured for implantation in a patient, wherein the body defines a chamber, wherein the body includes a nipple in fluid communication with the chamber, wherein the nipple is configured to couple with a conduit;
    (b) a septum associated with the body, wherein the septum is in communication with the chamber; and
    (c) a plurality of fasteners integral with the body, wherein the fasteners are movable relative to the body from a non-deployed position to a deployed position, wherein the fasteners are configured to substantially secure the body relative to tissue when the fasteners are in the deployed position, and further wherein the fasteners comprise swiveling hooks.

2. The apparatus of claim 1, further comprising a conduit coupled with the nipple, such that the conduit is in fluid communication with the chamber.

3. The apparatus of claim 2, further comprising an inflatable member coupled with the conduit, such that the inflatable member is in fluid communication with the chamber.

4. The apparatus of claim 3, wherein the inflatable member is part of a gastric band.

5. The apparatus of claim 1, wherein the body includes a housing and a metal base member.

6. The apparatus of claim 5, wherein the chamber has an upper boundary and a lower boundary, wherein the septum defines the upper boundary, wherein the metal base member defines the lower boundary.

7. The apparatus of claim 5, wherein the nipple extends through the metal base member.

8. The apparatus of claim 1, wherein the body defines a central region, wherein the fasteners are each rotatable about respective axes extending radially outwardly from the central region.

9. The apparatus of claim 1, wherein the fasteners are movable simultaneously.

10. The apparatus of claim 1, wherein the body includes an outwardly extending flange.

11. The apparatus of claim 10, wherein the fasteners are carried by the flange.

12. The apparatus of claim 11, wherein the flange defines a plurality of slots, wherein each fastener is disposed in a respective slot of the plurality of slots.

13. The apparatus of claim 1, further comprising an applicator configured to removably engage the body.

14. The apparatus of claim 13, wherein the applicator includes a rotatable member, wherein the rotatable member is rotatable to selectively move the fasteners relative to the body from the non-deployed position to the deployed position.

15. The apparatus of claim 14, wherein the rotatable member is operable to push the fasteners relative to the body from the non-deployed position to the deployed position upon rotation of the rotatable member.

16. The apparatus of claim 13, wherein the applicator is configured to hold the body when the fasteners are in the non-deployed position, wherein the applicator is configured to release the body upon deployment of the fasteners.

17. The apparatus of claim 13, wherein the applicator includes a first member configured to removably engage the body and a second member movable relative to the first member, wherein the applicator is operable to selectively move the fasteners relative to the body from the non-deployed position to the deployed position in response to longitudinal movement of the second member relative to the first member.

18. An apparatus, comprising:
(a) a body sized and configured for implantation in a patient, wherein the body defines a chamber and a central region, wherein the body includes a nipple in fluid communication with the chamber, wherein the nipple is configured to couple with a conduit;
(b) a septum associated with the body, wherein the septum is in communication with the chamber;
(c) a plurality of fasteners integral with the body, wherein the fasteners are each rotatable about respective axes extending radially outwardly from the central region to thereby move relative to the body from a non-deployed position to a deployed position, wherein the fasteners are configured to substantially secure the body relative to tissue when the fasteners are in the deployed position;
(d) a conduit coupled with the nipple such that the conduit is in fluid communication with the chamber; and
(e) an inflatable member coupled with the conduit, such that the inflatable member is in fluid communication with the chamber.

19. An apparatus, comprising:
(a) a body sized and configured for implantation in a patient, wherein the body defines a chamber;
(b) a plurality of fasteners integral with the body, wherein the fasteners are movable relative to the body from a non-deployed position to a deployed position, wherein the fasteners are configured to substantially secure the body relative to tissue when the fasteners are in the deployed position
(c) a conduit in fluid communication with the chamber; and
(d) a gastric band in fluid communication with the conduit.

\* \* \* \* \*